(12) United States Patent
Mosrin et al.

(10) Patent No.: US 10,961,220 B2
(45) Date of Patent: Mar. 30, 2021

(54) METHOD FOR PREPARING SUBSTITUTED IMIDAZOLYL CARBOXYAMIDES

(71) Applicant: BAYER AKTIENGESELLSCHAFT, Leverkusen (DE)

(72) Inventors: Marc Mosrin, Cologne (DE); Matthieu Willot, Duesseldorf (DE); Johannes-Rudolf Jansen, Monheim (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 16/613,374

(22) PCT Filed: May 8, 2018

(86) PCT No.: PCT/EP2018/061827
§ 371 (c)(1),
(2) Date: Nov. 13, 2019

(87) PCT Pub. No.: WO2018/210625
PCT Pub. Date: Nov. 22, 2018

(65) Prior Publication Data
US 2020/0172511 A1 Jun. 4, 2020

(30) Foreign Application Priority Data
May 15, 2017 (EP) .................. 17171039.5

(51) Int. Cl.
*C07D 401/12* (2006.01)
(52) U.S. Cl.
CPC .................. *C07D 401/12* (2013.01)
(58) Field of Classification Search
CPC .................................. C07D 401/12
See application file for complete search history.

(56) References Cited

U.S. PATENT DOCUMENTS 10,368,545 B2   8/2019  Fischer et al.
2019/0307126 A1  10/2019  Fischer et al.

FOREIGN PATENT DOCUMENTS

WO    2011/009804 A2   1/2011
WO    2016/128298 A1   8/2016

OTHER PUBLICATIONS

Dorwald, Side Reactions in Organic Synthesis, 2005, Wiley: VCH Weinhelm Preface, pp. 1-5 & Chapter 8, pp. 279-308.*

(Continued)

*Primary Examiner* — Patricia L Morris

(74) *Attorney, Agent, or Firm* — McBee Moore & Vanik IP, LLC

(57) ABSTRACT

The present invention relates to a method for preparing substituted imidazolyl carboxyamides of the formula (II)

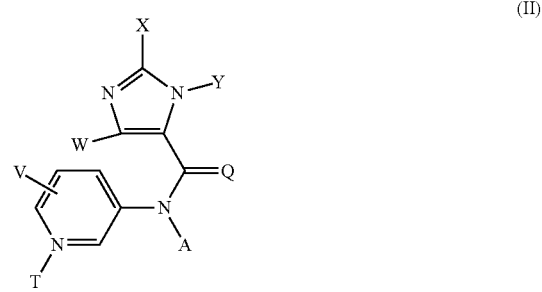

proceeding from compounds of the formula (I)

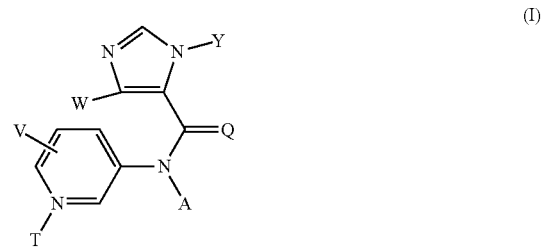

via an intermediate of the formula (IIIa) or (IIIb)

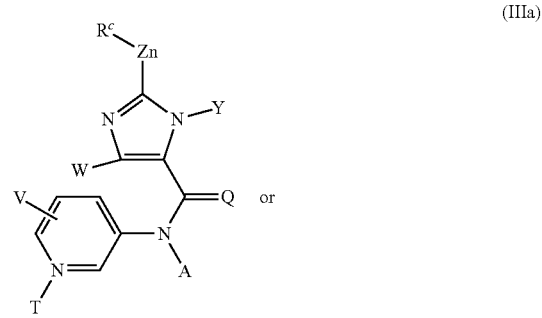

(Continued)

-continued

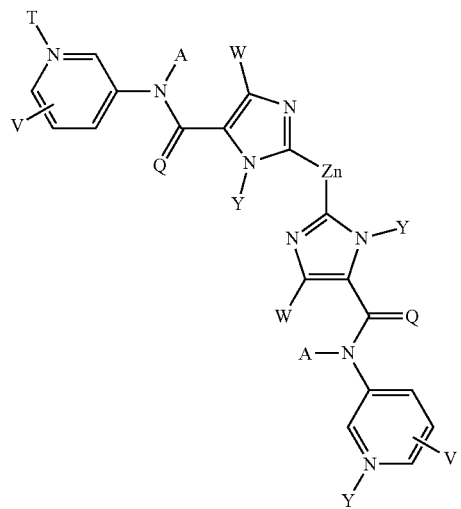

(IIIb)

in which the structural elements specified in the formulae (I), (II), (IIIa) and (IIIb) have the definitions stated. Furthermore, the invention relates to the compounds of the formulae (IIIa) and (IIIb).

8 Claims, No Drawings

(56) References Cited

OTHER PUBLICATIONS

International Search Report of International Patent Application No. PCT/EP2018/061827 dated Jul. 6, 2018.
Knochel, Paul, "(tmp)2Zn•2MgCl2•2LiCl: eine chemoselektive Base für die gezielte Zinkierung von empfindlichen Arenen und Heteroarenen", Angewandte Chemie International Edition, Aug. 27, 2007, pp. 7829-7832, vol. 119, No. 40.
Crestey, Francois et al., "Regioselective Functionalization of Purine Derivatives at Positions 8 and 6 Using Hindered TMP-Amide Bases of Zn and Mg", Synthesis, Oct. 22, 2013, pp, 3029-3037, vol. 45, No. 21.
Negishi, Ei-ichi et al., "Highly Satisfactory Alkynylation of Alkenyl Halides via Pd-Catalyzed Cross-Coupling with Alkynylzincs and Its Critical Comparison with the Sonogashira Alkynylation", Organic Letters, 2003, pp, 1597-1600, vol. 5, No. 10.
European Search Report of Euopean Application No. 17171039.5 dated Jul. 17, 2017.

* cited by examiner

METHOD FOR PREPARING SUBSTITUTED IMIDAZOLYL CARBOXYAMIDES

CROSS-REFERENCE TO RELATED APPLICATIONS

This application is a National Stage entry of International Application No. PCT/EP2018/061827, filed 8 May 2018, which claims priority to European Patent Application No. 17171039.5, filed 15 May 2017.

BACKGROUND

Field

The present invention relates to a method for preparing substituted imidazolyl carboxyamides of the formula (II)

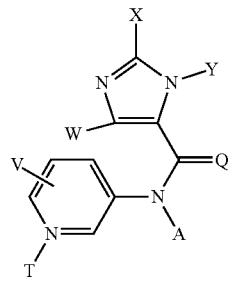

(II)

proceeding from compounds of the formula (I)

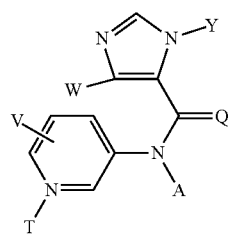

(I)

via an intermediate of the formula (IIIa) or (IIIb)

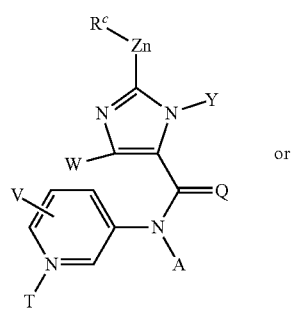

(IIIa)

or

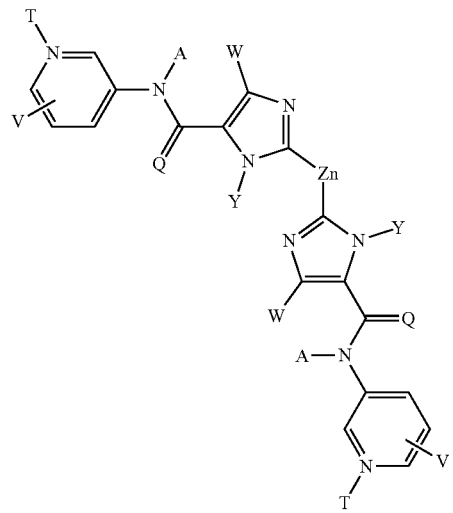

(IIIb)

in which the structural elements specified in the formulae (I), (II), (IIIa) and (IIIb) have the definitions given below.

Description of Related Art

Substituted imidazolyl carboxyamides of the formula (II) are of major industrial significance for the pharmaceutical and agrochemical industry and are important intermediates, for example, for compounds which are effective, inter alia, as pesticides or are themselves effective, inter alia, as pesticides.

Substituted imidazolyl carboxyamides of the formula (II) for use as pesticides and methods for the preparation thereof are described by way of example in WO 2011/009804 A2 and WO 2016/128298 A1.

The preparation methods that have been described in the prior art however include methods that are not economically implementable from an industrial point of view and/or have other disadvantages.

In particular, the regioselective introduction of the substituent X to compounds of the formula (II) represents a major challenge. This is made particularly difficult due to the amide group adjacent to the imidazolyl radical. This typically directs substituents preferably into the undesired ortho position. In addition, the amide group generally activates the ortho position on the likewise adjacent pyridyl radical. Therefore, this makes a targeted substitution at the desired position difficult.

In the case of lithium bases and magnesium bases in particular, disadvantages are the low chemical yields, performing at very low temperatures and the difficult regio- and chemoselectivity of the deprotonation due to the high reactivity of these reagents. Sometimes a transmetallation with zinc salts, such as zinc chloride for example, is still necessary in order to carry out further selective reactions such as Negishi cross couplings as described in Organic Letters 2003 (5), p. 1597ff. The preparation is therefore in two stages and unsuitable for industrial scale commercial processes.

With regard to the disadvantages outlined above, there is an urgent need for a simplified, industrially and economically performable method for preparing substituted imidazolyl carboxyamides of the formula (II). The substituted imidazolyl carboxyamides obtainable by this method sought are preferably to be obtained with good yield, high purity and in an economic manner.

SUMMARY

It has been found, surprisingly, that substituted imidazolyl carboxyamides of the formula (II) can be prepared advantageously in a method using an organozinc base, in particular even with high regio- and chemoselectivity and good yield.

The present invention accordingly provides a method for preparing compounds of the formula (II)

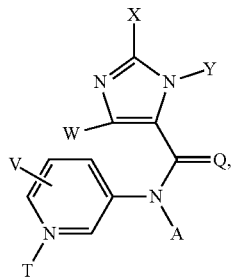

(II)

in which (configuration 1)

Q is oxygen or sulfur,

A is a radical from the group of hydrogen; $C_1$-$C_6$-alkyl, $C_3$-$C_6$-alkenyl or $C_3$-$C_6$-alkynyl, optionally mono- to polysubstituted independently of one another by halogen, $C_1$-$C_4$-alkoxy, $C_1$-$C_4$-alkyl-S(O)$_m$— or cyano; and $C_3$-$C_6$-cycloalkyl, optionally mono- or disubstituted independently of one another by halogen, $C_1$-$C_4$-alkyl, $C_1$-$C_4$-haloalkyl, $C_1$-$C_4$-alkoxy or cyano; and straight-chain or branched $C_3$-$C_8$-cycloalkyl-$C_1$-$C_4$-alkyl, optionally mono- or disubstituted independently of one another by halogen, $C_1$-$C_4$-alkyl, $C_1$-$C_4$-haloalkyl, $C_1$-$C_4$-alkoxy or cyano, V is a radical from the group of hydrogen, halogen, $C_1$-$C_4$-alkyl, $C_1$-$C_4$-haloalkyl, $C_1$-$C_4$-alkoxy, $C_1$-$C_4$-haloalkoxy and cyano, T is oxygen or an electron pair, W is a radical from the group of hydrogen, halogen, $C_1$-$C_4$-alkyl, $C_1$-$C_4$-haloalkyl, $C_1$-$C_4$-alkoxy, $C_1$-$C_4$-haloalkoxy and cyano, Y is a radical from the group of hydrogen, cyano; $C_1$-$C_6$-alkyl, $C_3$-$C_6$-alkenyl or $C_3$-$C_6$-alkynyl, optionally mono- to polysubstituted independently of one another by halogen, $C_1$-$C_4$-alkoxy, $C_1$-$C_4$-alkyl-S(O)$_m$— or cyano; $C_3$-$C_6$-cycloalkyl, optionally mono- or disubstituted independently of one another by halogen, $C_1$-$C_4$-alkyl, $C_1$-$C_4$-haloalkyl, $C_1$-$C_4$-alkoxy or cyano; straight-chain or branched $C_3$-$C_8$-cycloalkyl-$C_1$-$C_4$-alkyl, optionally interrupted once or twice independently of one another by O, S(O)$_m$, CO or NR$^2$ and optionally mono- to tetrasubstituted independently of one another by halogen, $C_1$-$C_4$-alkyl, $C_1$-$C_4$-haloalkyl, $C_1$-$C_4$-alkoxy or cyano; and arylalkyl or hetarylalkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro or cyano, m is a number 0, 1 or 2, R$^2$ is a radical from the group of hydrogen; $C_1$-$C_8$-alkyl, $C_3$-$C_8$-alkenyl or $C_3$-$C_8$-alkynyl, optionally mono- to polysubstituted independently of one another by halogen, $C_1$-$C_4$-alkoxy or $C_1$-$C_4$-alkyl-S(O)$_m$—; $C_3$-$C_8$-cycloalkyl, optionally interrupted once by O or S(O)$_m$ and optionally mono- or disubstituted independently of one another by halogen, $C_1$-$C_4$-alkyl, $C_1$-$C_4$-haloalkyl, $C_1$-$C_4$-alkoxy or cyano; straight-chain or branched $C_3$-$C_8$-cycloalkyl-$C_1$-$C_4$-alkyl, optionally interrupted once by O or S(O)$_m$ and optionally mono- or disubstituted independently of one another by halogen, $C_1$-$C_4$-alkyl, $C_1$-$C_4$-haloalkyl, $C_1$-$C_4$-alkoxy or cyano; aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro or cyano; and straight-chain or branched aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_m$—, $C_1$-$C_4$-haloalkoxy, $C_1$-$C_4$-haloalkyl-S(O)$_m$—, nitro or cyano, and X is a radical from the group of halogen, C(O)L$^1$, C(O)OL$^1$, C(O)NL$^2$L$^3$, $C_2$-$C_6$-alkenyl or $C_2$-$C_6$-alkynyl, mono- to pentasubstituted by fluorine, chlorine and bromine and mono- to trisubstituted by methoxy, ethoxy, methyl-S(O)$_n$—, ethyl-S(O)$_n$— and cyano, aryl or hetaryl, optionally mono- to trisubstituted independently of one another by halogen, NL$^2$L$^3$, nitro, cyano, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, $C_1$-$C_4$-alkylcarboxy, aryl or hetaryl; or is an aryl or hetaryl ring which, on two adjacent ring positions, is bonded to a chain consisting of one or two heteroatoms from the group of N, S or O and/or one to five carbon atoms and this forms in this case an optionally partially unsaturated aliphatic, aromatic, heteroaromatic or optionally partially unsaturated heterocyclic ring, and straight-chain or branched aryl-$C_1$-$C_4$-alkyl or hetaryl-$C_1$-$C_4$-alkyl, optionally mono- to trisubstituted independently of one another by halogen, NL$^2$L$^3$, nitro, cyano, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, carboxyl, aryl or hetaryl, wherein L$^1$ is $C_1$-$C_8$-alkyl, $C_2$-$C_8$-alkenyl or $C_2$-$C_8$-alkynyl, optionally mono- to polysubstituted independently of one another by halogen, cyano, $C_1$-$C_4$-alkoxy or $C_1$-$C_4$-alkyl-S(O)$_n$—; $C_3$-$C_8$-cycloalkyl, optionally interrupted once by O or S(O) and optionally mono- or disubstituted independently of one another by halogen, $C_1$-$C_4$-alkyl, $C_1$-$C_4$-haloalkyl, $C_1$-$C_4$-alkoxy or cyano; straight-chain or branched $C_3$-$C_8$-cycloalkyl-$C_1$-$C_4$-alkyl, optionally interrupted once by O or S(O) and optionally mono- or disubstituted independently of one another by halogen, $C_1$-$C_4$-alkyl, $C_1$-$C_4$-haloalkyl, $C_1$-$C_4$-alkoxy or cyano; aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano; and straight-chain or branched aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano, $L^2$ is a radical from the group of hydrogen; $C_1$-$C_4$-alkyl, $C_3$-$C_6$-alkenyl or $C_3$-$C_6$-alkynyl, optionally mono- to polysubstituted independently of one another by halogen, $C_1$-$C_4$-alkoxy, $C_1$-$C_4$-alkyl-S(O)$_n$— or cyano; $C_3$-$C_6$-cycloalkyl, $C_1$-$C_4$-alkylsulfonyl, $C_3$-$C_6$-cycloalkylsulfonyl, $C_1$-$C_4$-alkylcarbonyl or $C_1$-$C_4$-alkoxycarbonyl, optionally mono- or disubstituted independently of one another by halogen, $C_1$-$C_4$-alkyl, $C_1$-$C_4$-haloalkyl, $C_1$-$C_4$-alkoxy or cyano; and is phenyl-$C_1$-$C_2$-alkoxycarbonyl, optionally mono- or disubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, difluoromethoxy, trifluoromethoxy, trifluoromethyl-S(O)$_n$—, difluoroethyl-S(O)$_n$—, trifluoroethyl-S(O)$_n$—, nitro or cyano, $L_3$ is a radical from the group of hydrogen; $C_1$-$C_4$-alkyl, $C_3$-$C_6$-alkenyl, $C_3$-$C_6$-alkynyl or $C_1$-$C_4$-alkoxy, optionally mono- to polysubstituted independently of one another by halogen, hydroxyl, $C_1$-$C_4$-alkoxy, $C_1$-$C_4$-alkoxycarbonyl, $C_1$-$C_4$-alkyl-S(O)$_n$— or cyano; straight-chain or branched $C_3$-$C_8$-cycloalkyl or $C_3$-$C_8$-cycloalkyl-$C_1$-$C_4$-alkyl, optionally interrupted once or twice independently of one another by O, S(O)$_n$, CO or NR$^4$ and optionally mono- to tetrasubstituted independently of one another by halogen, $C_1$-$C_4$-alkyl, $C_1$-$C_4$-haloalkyl, $C_1$-$C_4$-alkoxy or cyano; aryl, hetaryl, arylalkyl or hetarylalkyl, optionally mono- to trisubstituted independently of one another by halogen, $C_1$-$C_4$-alkyl, $C_1$-$C_4$-haloalkyl, hydroxyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano, or $L^2$ and $L^3$ together form a four- to seven-membered aliphatic ring which is optionally mono- to trisubstituted by halogen, $C_1$-$C_4$-alkyl or $C_1$-$C_4$-alkoxy and optionally comprises an N, S or O atom, $R^4$ is a radical from the group of hydrogen; $C_1$-$C_8$-alkyl, $C_3$-$C_8$-alkenyl and $C_3$-$C_8$-alkynyl, optionally mono- to trisubstituted independently of one another by halogen, $C_1$-$C_4$-alkoxy and $C_1$-$C_4$-alkyl-S(O)$_n$—; $C_3$-$C_8$-cycloalkyl and $C_3$-$C_8$-cycloalkyl-$C_1$-$C_4$-alkyl, optionally mono- or disubstituted independently of one another by halogen, $C_1$-$C_4$-alkyl, $C_1$-$C_4$-haloalkyl, $C_1$-$C_4$-alkoxy and cyano; aryl and hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro and cyano; straight-chain or branched aryl-$C_1$-$C_4$-alkyl and hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro and cyano, and n is a number 0, 1 or 2, characterized in that, in a first method step a), a compound of the formula (I)

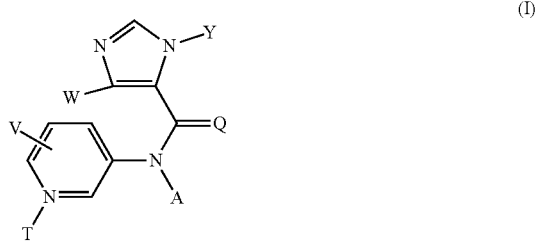

(I)

in which Q, A, V, T, W and Y each have the definitions given above, is reacted with an organozinc base of the structure (NR$^a$R$^b$)—Zn—R$^c$ or (NR$^a$R$^b$)$_2$—Zn, in which R$^c$ is halogen or —O-pivaloyl and R$^a$ and R$^b$ together form a —(CH$_2$)$_4$—, —(CH$_2$)$_5$— or —(CH$_2$)$_2$O(CH$_2$)$_2$— group, where each of these groups may optionally be substituted by 1, 2, 3 or 4 R$^d$ radicals and R$^d$ is selected from the group consisting of methyl, ethyl, n-propyl and isopropyl, to give a compound of the formula (IIIa) or (IIIb),

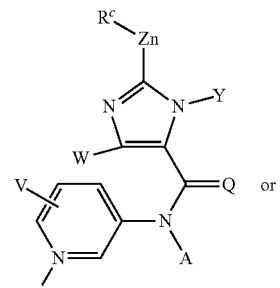

(IIIa)

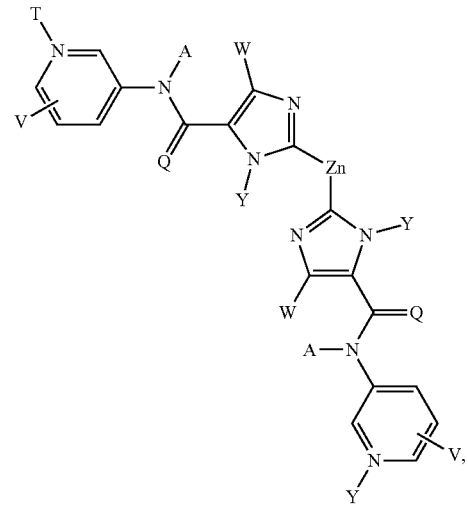

(IIIb)

in which Q, A, V, T, W, Y and R$^c$ each have the definitions given above, and this compound of the formula (IIIa) or (IIIb) is reacted in a second method step b) with a compound of the structure X—Z, in which Z is halogen and X has the aforementioned definition to give the compound of the formula (II).

DETAILED DESCRIPTION OF A PREFERRED EMBODIMENT

Here, Z is preferably chlorine, bromine, iodine or fluorine, particularly preferably bromine or iodine, and especially preferably iodine.

The compounds of the formulae (I), (II), (IIIa) and (IIIb) may also be present as salts in the method according to the invention.

The compounds of the formulae (IIIa) and (IIIb) and the organozinc base may also be present complexed with salts, where the salts are preferably alkali metal halides or alkaline earth metal halides, preferably lithium chloride and/or magnesium chloride and particularly preferably lithium chloride.

Preferred and particularly preferred definitions of the A, V, T, W, Y, X and $R^c$ radicals included in the aforementioned formulae (I), (II), (IIIa) and (IIIb) of the method according to the invention are elucidated hereinafter, with more specific description of the organozinc base further down, and so the preferred configurations of the base are specified at that point.

In the following, compounds of the formula (III) are synonymous with compounds of the formula (IIIa) or (IIIb).

(Configuration 2)

For the compounds of the formula (I), (II) and (III), it is preferable that

Q is oxygen or sulfur,

A is a radical from the group of hydrogen; $C_1$-$C_6$-alkyl, $C_3$-$C_6$-alkenyl or $C_3$-$C_6$-alkynyl, optionally mono- to pentasubstituted independently of one another by fluorine, chlorine, bromine, methoxy, ethoxy, methyl-$S(O)_m$—, ethyl-$S(O)_m$— or cyano; $C_3$-$C_6$-cycloalkyl, optionally mono- or disubstituted independently of one another by fluorine, chlorine, bromine, methyl, ethyl, trifluoromethyl, methoxy, ethoxy or cyano; and straight-chain or branched $C_3$-$C_6$-cycloalkyl-$C_1$-$C_2$-alkyl, optionally mono- or disubstituted independently of one another by fluorine, chlorine, bromine, methyl, ethyl, trifluoromethyl, methoxy, ethoxy or cyano, V is a radical from the group of hydrogen, fluorine, chlorine, bromine, methyl, ethyl, difluoromethyl, trifluoromethyl, methoxy, ethoxy, difluoromethoxy, trifluoromethoxy and cyano, T is oxygen or an electron pair, W is a radical from the group of hydrogen, fluorine, chlorine, bromine, methyl, ethyl, difluoromethyl, trifluoromethyl, methoxy, ethoxy, difluoromethoxy, trifluoromethoxy and cyano, Y is a radical from the group of hydrogen, cyano; $C_1$-$C_4$-alkyl, $C_3$-$C_4$-alkenyl or $C_3$-$C_4$-alkynyl, optionally mono- to pentasubstituted independently of one another by fluorine, chlorine, bromine, methoxy, ethoxy, methyl-$S(O)_m$—, ethyl-$S(O)_m$— or cyano; $C_3$-$C_6$-cycloalkyl, optionally mono- or disubstituted independently of one another by fluorine, chlorine, bromine, methyl, ethyl, trifluoromethyl, methoxy, ethoxy or cyano; and straight-chain or branched $C_3$-$C_6$-cycloalkyl-$C_1$-$C_2$-alkyl, optionally interrupted once or twice independently of one another by O, $S(O)_m$, CO or $NR^2$ and optionally mono- to tetrasubstituted independently of one another by fluorine, chlorine, bromine, methyl, ethyl, trifluoromethyl, methoxy, ethoxy or cyano, m is a number 0, 1 or 2, $R^2$ is a radical from the group of hydrogen; $C_1$-$C_6$-alkyl, $C_3$-$C_6$-alkenyl or $C_3$-$C_6$-alkynyl, optionally mono- to pentasubstituted independently of one another by fluorine, chlorine, bromine, methoxy, ethoxy, methyl-$S(O)_m$— or ethyl-$S(O)_m$—; $C_3$-$C_6$-cycloalkyl, optionally interrupted once by O or $S(O)_m$ and optionally mono- or disubstituted independently of one another by fluorine, chlorine, bromine, methyl, ethyl, trifluoromethyl, methoxy, ethoxy or cyano; straight-chain or branched $C_3$-$C_6$-cycloalkyl-$C_1$-$C_2$-alkyl, optionally interrupted once by O or $S(O)_m$ and optionally mono- or disubstituted independently of one another by fluorine, chlorine, bromine, methyl, ethyl, trifluoromethyl, methoxy, ethoxy or cyano; phenyl or pyridyl, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_m$—, difluoroethyl-$S(O)_m$—, trifluoroethyl-$S(O)_m$—, nitro or cyano; and straight-chain or branched phenyl-$C_1$-$C_2$-alkyl, pyridyl-$C_1$-$C_2$-alkyl, pyrimidyl-$C_1$-$C_2$-alkyl or thiazolyl-$C_1$-$C_2$-alkyl, optionally mono- or disubstituted independently of one another by fluorine, chlorine, bromine, methyl, ethyl, difluoromethyl, trifluoromethyl, methoxy, ethoxy, methyl-$S(O)_m$—, ethyl-$S(O)_m$—, difluoromethoxy, trifluoromethoxy, trifluoromethyl-$S(O)_m$—, difluoroethyl-$S(O)_m$—, trifluoroethyl-$S(O)_m$—, nitro or cyano, X is a radical from the group of halogen, $C(O)L^1$, $C(O)OL^1$, $C(O)NL^2L^3$, $C_2$-$C_8$-alkenyl or $C_2$-$C_8$-alkynyl, optionally mono- to pentasubstituted by halogen and mono- or disubstituted by $C_1$-$C_4$-alkoxy, $C_1$-$C_4$-alkyl-$S(O)_n$— and cyano, aryl or hetaryl optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, $C_1$-$C_4$-alkylcarboxy, $NL^2L^3$, nitro, cyano or aryl or hetaryl, which is optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, nitro or cyano; or is an aryl or hetaryl ring which, on two adjacent ring positions, is bonded to a chain consisting of one or two heteroatoms from the group of N, S or O and one or two carbon atoms and this forms in this case a heteroaromatic or optionally partially unsaturated heterocyclic ring, and straight-chain or branched aryl-$C_1$-$C_4$-alkyl or hetaryl-$C_1$-$C_4$-alkyl substituted by aryl or hetaryl optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, $C_1$-$C_4$-alkylcarboxy, $NL^2L^3$, nitro, cyano or optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, nitro or cyano, wherein $L^1$ is a radical from the group of $C_1$-$C_6$-alkyl, $C_3$-$C_6$-alkenyl or $C_3$-$C_6$-alkynyl, optionally mono- to pentasubstituted independently of one another by fluorine, chlorine, bromine, methoxy, ethoxy or cyano; and $C_3$-$C_6$-cycloalkyl, optionally mono- or disubstituted independently of one another by fluorine, chlorine, bromine, methyl, ethyl, trifluoromethyl, methoxy, ethoxy or cyano; is phenyl, pyridyl, pyrimidinyl or thienyl, optionally mono- or disubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, difluoromethoxy, trifluoromethoxy, trifluoromethyl-$S(O)_n$—, difluoroethyl-$S(O)_n$—, trifluoroethyl-$S(O)_n$—, nitro or cyano; is straight-chain or branched phenyl-$C_1$-$C_2$-alkyl or pyridyl-$C_1$-$C_2$-alkyl, optionally mono- or disubstituted independently of one another by fluorine, chlorine, bromine, methyl, ethyl, difluoromethyl, trifluoromethyl, methoxy, ethoxy, Me-$S(O)_n$—, Et-$S(O)_n$—, difluoromethoxy, trifluoromethoxy, trifluoromethyl-$S(O)_n$—, difluoroethyl-$S(O)_n$—, trifluoroethyl-$S(O)_n$—, nitro or cyano, $L^2$ is a radical from the group of hydrogen; $C_1$-$C_4$-alkyl, $C_3$-$C_4$-alkenyl or $C_3$-$C_4$-alkynyl, optionally mono- to trisubstituted independently of one another by fluorine or chlorine; $C_3$-$C_6$-cycloalkyl, optionally mono- or disubstituted independently of one another by fluorine, chlorine, methyl, ethyl, trifluoromethyl, methoxy, ethoxy or cyano; or is $C_1$-$C_4$-alkylcarbonyl or $C_1$-$C_4$-alkoxycarbonyl, optionally mono- to trisubstituted independently of one another by fluorine, chlorine, methoxy or ethoxy; and is phenyl-$C_1$-$C_2$-alkoxycarbonyl, optionally mono- or disubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, difluoromethoxy, trifluoromethoxy, trifluoromethyl-S(O)$_n$—, difluoroethyl-S(O)$_n$—, trifluoroethyl-S(O)$_n$—, nitro or cyano, $L^3$ is a radical from the group of hydrogen; $C_1$-$C_4$-alkyl, $C_3$-$C_6$-alkenyl, $C_3$-$C_6$-alkynyl or $C_1$-$C_4$-alkoxy, optionally mono- to trisubstituted independently of one another by halogen, methoxy, ethoxy, n- or isopropoxy or methyl-S(O)$_n$—; $C_3$-$C_6$-cycloalkyl or $C_3$-$C_6$-cycloalkyl-$C_1$-$C_4$-alkyl, optionally mono- or disubstituted independently of one another by fluorine, chlorine, methyl, ethyl, trifluoromethyl, methoxy, ethoxy or cyano; phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl or thiadiazolyl, optionally mono- or disubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, difluoromethoxy, trifluoromethoxy, trifluoromethyl-S(O)$_n$—, difluoroethyl-S(O)$_n$—, trifluoroethyl-S(O)$_n$—, nitro or cyano; straight-chain or branched phenyl-$C_1$-$C_2$-alkyl or pyridyl-$C_1$-$C_2$-alkyl, optionally mono- or disubstituted independently of one another by fluorine, chlorine, bromine, methyl, ethyl, difluoromethyl, trifluoromethyl, methoxy, ethoxy, Me-S(O)$_n$—, Et-S(O)$_n$—, difluoromethoxy, trifluoromethoxy, trifluoromethyl-S(O)$_n$—, difluoroethyl-S(O)$_n$—, trifluoroethyl-S(O)$_n$—, nitro or cyano, or $L^2$ and $L^3$ together form a four- to six-membered aliphatic ring which optionally comprises an N, S or O atom and is optionally mono- or disubstituted by fluorine, chlorine, bromine, methyl, ethyl, methoxy or ethoxy and n is a number 0, 1 or 2 and $R^c$ is —O-pivaloyl, chlorine, bromine or iodine.

(Configuration 3)

For the compounds of the formula (I), (II) and (III), it is particularly preferable that Q is oxygen or sulfur, A is a radical from the group of hydrogen; methyl, ethyl, propyl, allyl, propargyl, cyclopropyl or cyclopropylmethyl, optionally mono- to trisubstituted independently of one another by fluorine, methoxy, ethoxy or cyano, V is a radical from the group of hydrogen, fluorine, chlorine, methyl and cyano, T is oxygen or an electron pair, W is a radical from the group of hydrogen, fluorine, chlorine, bromine, methyl, ethyl and cyano, Y is a radical from the group of hydrogen, benzyl; and methyl, ethyl, propyl, allyl or propargyl, optionally mono- to trisubstituted independently of one another by fluorine, methoxy, ethoxy or cyano, X is a radical from the group of halogen, C(O)$L^1$, C(O)O$L^1$, C(O)N$L^2L^3$, vinyl, allyl, methallyl, 2-butenyl, propargyl, ethynyl and 2-butynyl, optionally mono- to trisubstituted independently of one another by fluorine, chlorine and bromine and/or monosubstituted by methoxy, ethoxy, methylsulfanyl, ethylsulfanyl, methylsulfinyl, ethylsulfinyl, methylsulfonyl, ethylsulfonyl or cyano, aryl or hetaryl, substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano or is an aryl or hetaryl ring which, on two adjacent ring positions, is bonded to a chain consisting of one or two oxygen atoms and one or two carbon atoms and this forms in this case a heteroaromatic or optionally partially unsaturated heterocyclic ring, and straight-chain or branched aryl-$C_1$-$C_4$-alkyl or hetaryl-$C_1$-$C_4$-alkyl substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano, wherein $L^1$ is a radical from the group of $C_1$-$C_6$-alkyl, optionally mono- to pentasubstituted independently of one another by fluorine, chlorine, bromine, methoxy, ethoxy or cyano; phenylmethyl, optionally mono- or disubstituted independently of one another by fluorine, chlorine, bromine, methyl, ethyl, difluoromethyl, trifluoromethyl, methoxy, ethoxy, Me-S(O)$_n$—, Et-S(O)$_n$—, difluoromethoxy, trifluoromethoxy, trifluoromethyl-S(O)$_n$—, difluoroethyl-S(O)$_—$, trifluoroethyl-S(O)$_n$—, nitro or cyano, or is $C_3$-$C_6$-cycloalkyl, L² is a radical from the group of hydrogen; $C_1$-$C_4$-alkyl, $C_1$-$C_4$-alkylsulfonyl, $C_3$-$C_6$-cycloalkylsulfonyl, $C_1$-$C_4$-alkylcarbonyl or $C_1$-$C_4$-alkoxycarbonyl, optionally mono- to trisubstituted independently of one another by fluorine, chlorine, methoxy or ethoxy; and arylmethoxycarbonyl, optionally mono- to trisubstituted independently of one another by fluorine, chlorine, bromine, methyl, ethyl, trifluoromethyl, methoxy or ethoxy, L³ is a radical from the group of hydrogen; $C_1$-$C_4$-alkyl, $C_3$-$C_6$-alkenyl, $C_3$-$C_6$-alkynyl or $C_1$-$C_4$-alkoxy, optionally mono- to trisubstituted independently of one another by halogen, hydroxyl, methoxy, ethoxy, methoxycarbonyl, ethoxycarbonyl or cyano; $C_3$-$C_6$-cycloalkyl or $C_3$-$C_6$-cycloalkyl-$C_1$-$C_4$-alkyl, optionally mono- or disubstituted independently of one another by fluorine, chlorine, methyl, ethyl, trifluoromethyl, methoxy, ethoxy or cyano; phenyl, pyridyl or thienyl, optionally mono- or disubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, trifluoromethoxy, nitro or cyano; phenyl-$C_1$-$C_2$-alkyl or pyridyl-$C_1$-$C_2$-alkyl, optionally mono- or disubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, trifluoromethoxy, nitro or cyano, or L² and L³ together form a four- to six-membered aliphatic ring which optionally comprises an N, S or O atom and is optionally mono- or disubstituted by fluorine, chlorine, bromine, methyl, ethyl, methoxy or ethoxy and n is a number 0, 1 or 2 and $R^c$ is —O-pivaloyl, chlorine, bromine or iodine.

(Configuration 4)

For the compounds of the formula (I), (II) and (III), it is especially preferable that Q is oxygen or sulfur, A is a radical from the group of hydrogen, methyl, ethyl, propyl, difluoroethyl, trifluoroethyl, methoxymethyl, ethoxymethyl, cyanomethyl, allyl, propargyl, cyclopropyl or cyclopropylmethyl, V is hydrogen or fluorine, T is oxygen or an electron pair, W is a radical from the group of hydrogen, fluorine, chlorine, bromine and methyl, Y is a radical from the group of hydrogen, methyl, ethyl, propyl, difluoroethyl, trifluoroethyl, methoxymethyl, ethoxymethyl, cyanomethyl and benzyl, X is a radical from the group of halogen, C(O)L¹, C(O)OL¹, C(O)NL²L³, vinyl, allyl, methallyl, 2-butenyl, propargyl, ethynyl and 2-butynyl, optionally mono- to trisubstituted independently of one another by fluorine, chlorine and bromine and/or monosubstituted by methoxy, ethoxy, methylsulfanyl, ethylsulfanyl, methylsulfinyl, ethylsulfinyl, methylsulfonyl, ethylsulfonyl or cyano, phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano or is a phenyl which, on two adjacent ring positions, is bonded to a chain consisting of one or two oxygen atoms and one or two carbon atoms and this forms in this case an optionally partially unsaturated heterocyclic ring and straight-chain or branched phenyl-$C_1$-$C_2$-alkyl, pyridyl-$C_1$-$C_2$-alkyl, pyrimidyl-$C_1$-$C_2$-alkyl, thiazolyl-$C_1$-$C_2$-alkyl and pyrazolyl-$C_1$-$C_2$-alkyl substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano, wherein L¹ is a radical from the group of methyl, ethyl, n- or isopropyl, 1-cyano-1-methylethyl or cyclopropyl, L² is a radical from the group of hydrogen, methyl, ethyl, methylsulfonyl, cyclopropylsulfonyl, methoxycarbonyl, ethoxycarbonyl, 2-methoxyethoxycarbonyl n-, iso, sec- or t-butoxycarbonyl, L³ is a radical from the group of hydrogen, methyl, ethyl, n- or isopropyl, n-, iso, sec- or tert-butyl, 2,2,2-trifluoroethyl, 2-hydroxyethyl, 2-methoxyethyl, cyanomethyl, methoxycarbonylmethyl, ethoxycarbonylmethyl, cyclopropyl, 1-cyanocyclopropyl, cyclopropylmethyl, cyclobutyl, cyclopentyl, cyclohexyl, methoxy, ethoxy, phenyl, 2-$C_1$-phenyl, 3-Cl-phenyl, 4-Cl-phenyl, pyridyl, phenylmethyl, 1-phenyl-2-hydroxyethyl, 2-$C_1$-phenylmethyl, 3-Cl-phenylmethyl, 4-Cl-phenylmethyl, or $L^2$ and $L^3$ together are $(CH_2)_5$, $(CH_2)_4$, $(CH_2)_3$ or $(CH_2)_2O(CH_2)_2$, and n is a number 0, 1 or 2 and $R^c$ is chlorine, bromine or iodine.

(Configuration 5)

For the compounds of the formula (I), (II) and (III), it is emphasized that

Q is oxygen,

A is a radical from the group of hydrogen, methyl, ethyl and cyclopropyl and is preferably methyl or ethyl, V is hydrogen, T is oxygen or an electron pair, preferably an electron pair, W is a radical from the group of hydrogen, methyl, fluorine, chlorine and bromine and is preferably hydrogen, Y is methyl or ethyl, X is a radical from the group of halogen, $C(O)L^1$, $C(O)OL^1$, $C(O)NL^2L^3$, vinyl, allyl, methallyl, 2-butenyl, propargyl, ethynyl and 2-butynyl, optionally mono- to trisubstituted independently of one another by fluorine, chlorine and bromine and/or monosubstituted by methoxy, ethoxy, methylsulfanyl, ethylsulfanyl, methylsulfinyl, ethylsulfinyl, methylsulfonyl, ethylsulfonyl or cyano, phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, cyclopropylmethyl-$S(O)_n$—, difluoromethoxy, trifluoromethoxy, trifluoromethyl-$S(O)_n$—, difluoroethyl-$S(O)_n$—, trifluoroethyl-$S(O)_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, cyclopropylmethyl-$S(O)_n$—, difluoromethoxy, trifluoromethoxy, trifluoromethyl-$S(O)_n$—, difluoroethyl-$S(O)_n$—, trifluoroethyl-$S(O)_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano or is a phenyl which, on two adjacent ring positions, is bonded to a chain consisting of one or two oxygen atoms and one or two carbon atoms and this forms in this case an optionally partially unsaturated heterocyclic ring and straight-chain or branched phenyl-$C_1$-$C_2$-alkyl, pyridyl-$C_1$-$C_2$-alkyl, pyrimidyl-$C_1$-$C_2$-alkyl, thiazolyl-$C_1$-$C_2$-alkyl and pyrazolyl-$C_1$-$C_2$-alkyl substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, cyclopropylmethyl-$S(O)_n$—, difluoromethoxy, trifluoromethoxy, trifluoromethyl-$S(O)_n$—, difluoroethyl-$S(O)_n$—, trifluoroethyl-$S(O)_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, cyclopropylmethyl-$S(O)_n$—, difluoromethoxy, trifluoromethoxy, trifluoromethyl-$S(O)_n$—, difluoroethyl-$S(O)_n$—, trifluoroethyl-$S(O)_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano, wherein $L^1$ is a radical from the group of methyl, ethyl, n- or isopropyl, 1-cyano-1-methylethyl or cyclopropyl, $L^2$ is a radical from the group of hydrogen, methyl, ethyl, methylsulfonyl or cyclopropylsulfonyl, $L^3$ is a radical from the group of hydrogen, methyl, ethyl, isopropyl, isobutyl, tert-butyl, 2,2,2-trifluoroethyl, 2-hydroxyethyl, 2-methoxyethyl, cyanomethyl, methoxycarbonylmethyl, ethoxycarbonylmethyl, cyclopropyl, 1-cyanocyclopropyl, cyclopentyl, cyclopropylmethyl, methoxy, ethoxy, phenyl, pyrid-3-yl, phenylmethyl, 1-phenyl-2-hydroxyethyl, or $L^2$ and $L^3$ together are $(CH_2)_5$, $(CH_2)_4$, $(CH_2)_3$ or $(CH_2)_2O(CH_2)_2$, and n is a number 0, 1 or 2 and $R^c$ is chlorine or bromine, preferably chlorine.

The radical definitions and elucidations given above apply both to the end products and intermediates and to the starting materials in a corresponding manner. These radical definitions can be combined with one another as desired, i.e. including combinations between the respective preferred ranges.

In the compounds of the formulae (I), (II) and (III), A is particularly advantageously methyl or ethyl and Q, V, T, W, Y, X and $R^c$ have the definitions according to configuration 1 or configuration 2 or configuration 3 or configuration 4 or configuration 5. (Configuration 6)

Furthermore, in the compounds of the formulae (I), (II) and (III), Q is particularly advantageously oxygen and A, V, T, W, Y, X and $R^c$ have the definitions according to configuration 1 or configuration 2 or configuration 3 or configuration 4. (Configuration 7)

Furthermore, in the compounds of the formulae (I), (II) and (III), V is particularly advantageously hydrogen and A, Q, T, W, Y, X and $R^c$ have the definitions according to configuration 1 or configuration 2 or configuration 3 or configuration 4. (Configuration 8)

Furthermore, in the compounds of the formulae (I), (II) and (III), T is particularly advantageously an electron pair and A, Q, V, W, Y, X and $R^c$ have the definitions according to configuration 1 or configuration 2 or configuration 3 or configuration 4 or configuration 5. (Configuration 9)

Furthermore, in the compounds of the formulae (I), (II) and (III), W is particularly advantageously hydrogen and A, Q, T, V, Y, X and $R^c$ have the definitions according to configuration 1 or configuration 2 or configuration 3 or configuration 4 or configuration 5.

(Configuration 10)

Furthermore, in the compounds of the formulae (I), (II) and (III), Y is particularly advantageously methyl or ethyl and A, Q, T, V, W, X and $R^c$ have the definitions according to configuration 1 or configuration 2 or configuration 3 or configuration 4. (Configuration 11)

Furthermore, in the compounds of the formulae (I), (II) and (III), $R^c$ is particularly advantageously chlorine or bromine and A, Q, T, V, Y, X and W have the definitions according to configuration 1 or configuration 2 or configuration 3 or configuration 4 or configuration 5. (Configuration 12)

Furthermore, in the compounds of the formulae (I), (II) and (III), $R^c$ is particularly advantageously chlorine and A, Q, T, V, Y, X and W have the definitions according to configuration 1 or configuration 2 or configuration 3 or configuration 4. (Configuration 13)

Furthermore, in the compounds of the formulae (I), (II) and (III), particularly advantageously Q is oxygen,
A is a radical from the group of methyl or ethyl,
V is hydrogen,
T is an electron pair,
W is hydrogen,
Y is methyl or ethyl,
$R^c$ is chlorine
and X has the definition according to configuration 1 or configuration 2 or configuration 3 or configuration 4 or configuration 5. (Configuration 14)

Furthermore, in the compounds of the formulae (I), (II) and (III), particularly advantageously X is a radical from the group of halogen, $C(O)L^1$, $C(O)OL^1$, $C(O)NL^2L^3$, $C_2$-$C_6$-alkenyl or $C_2$-$C_6$-alkynyl, mono- to pentasubstituted by fluorine, chlorine and bromine and mono- to trisubstituted by methoxy, ethoxy, methyl-$S(O)_n$—, ethyl-$S(O)_n$— and cyano, aryl or hetaryl, optionally mono- to trisubstituted independently of one another by halogen, $NL^2L^3$, nitro, cyano, $C_1$-$C_4$-alkyl, $C_1$-$C_4$-haloalkyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, $C_1$-$C_4$-alkylcarboxy, aryl or hetaryl; or is an aryl or hetaryl ring which, on two adjacent ring positions, is bonded to a chain consisting of one or two heteroatoms from the group of N, S or O and/or one to five carbon atoms and this forms in this case an optionally partially unsaturated aliphatic, aromatic, heteroaromatic or optionally partially unsaturated heterocyclic ring, and straight-chain or branched aryl-$C_1$-$C_4$-alkyl or hetaryl-$C_1$-$C_4$-alkyl, optionally mono- to trisubstituted independently of one another by halogen, $NL^2L^3$, nitro, cyano, $C_1$-$C_4$-alkyl, $C_1$-$C_4$-haloalkyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, carboxyl, aryl or hetaryl, wherein $L^1$ is $C_1$-$C_8$-alkyl, $C_2$-$C_8$-alkenyl or $C_2$-$C_8$-alkynyl, optionally mono- or polysubstituted independently of one another by halogen, cyano, $C_1$-$C_4$-alkoxy or $C_1$-$C_4$-alkyl-$S(O)_n$—; $C_3$-$C_8$-cycloalkyl, optionally interrupted once by O or $S(O)_n$ and optionally mono- to disubstituted independently of one another by halogen, $C_1$-$C_4$-alkyl, $C_1$-$C_4$-haloalkyl, $C_1$-$C_4$-alkoxy or cyano; straight-chain or branched $C_3$-$C_8$-cycloalkyl-$C_1$-$C_4$-alkyl, optionally interrupted once by O or $S(O)_n$ and optionally mono- or disubstituted independently of one another by halogen, $C_1$-$C_4$-alkyl, $C_1$-$C_4$-haloalkyl, $C_1$-$C_4$-alkoxy or cyano;

aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, nitro or cyano; and straight-chain or branched aryl-$C_1$-$C_4$-alkyl or hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, nitro or cyano, $L^2$ is a radical from the group of hydrogen; $C_1$-$C_4$-alkyl, $C_3$-$C_6$-alkenyl or $C_3$-$C_6$-alkynyl, optionally mono- or polysubstituted independently of one another by halogen, $C_1$-$C_4$-alkoxy, $C_1$-$C_4$-alkyl-$S(O)_n$— or cyano; $C_3$-$C_6$-cycloalkyl, $C_1$-$C_4$-alkylsulfonyl, $C_3$-$C_6$-cycloalkylsulfonyl, $C_1$-$C_4$-alkylcarbonyl or $C_1$-$C_4$-alkoxycarbonyl, optionally mono- or disubstituted independently of one another by halogen, $C_1$-$C_4$-alkyl, $C_1$-$C_4$-haloalkyl, $C_1$-$C_4$-alkoxy or cyano; and is phenyl-$C_1$-$C_2$-alkoxycarbonyl, optionally mono- or disubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, difluoromethoxy, trifluoromethoxy, trifluoromethyl-$S(O)_n$—, difluoroethyl-$S(O)_n$—, trifluoroethyl-$S(O)_n$—, nitro or cyano, $L_3$ is a radical from the group of hydrogen; $C_1$-$C_4$-alkyl, $C_3$-$C_6$-alkenyl, $C_3$-$C_6$-alkynyl or $C_1$-$C_4$-alkoxy, optionally mono- to polysubstituted independently of one another by halogen, hydroxyl, $C_1$-$C_4$-alkoxy, $C_1$-$C_4$-alkoxycarbonyl, $C_1$-$C_4$-alkyl-$S(O)_n$— or cyano; straight-chain or branched $C_3$-$C_8$-cycloalkyl or $C_3$-$C_8$-cycloalkyl-$C_1$-$C_4$-alkyl, optionally interrupted once or twice independently of one another by O, $S(O)_n$, CO or $NR^4$ and optionally mono- to tetrasubstituted independently of one another by halogen, $C_1$-$C_4$-alkyl, $C_1$-$C_4$-haloalkyl, $C_1$-$C_4$-alkoxy or cyano; aryl, hetaryl, arylalkyl or hetarylalkyl, optionally mono- to trisubstituted independently of one another by halogen, $C_1$-$C_4$-alkyl, $C_1$-$C_4$-haloalkyl, hydroxyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, nitro or cyano, or $L^2$ and $L^3$ together form a four- to seven-membered aliphatic ring which is optionally mono- to trisubstituted by halogen, $C_1$-$C_4$-alkyl or $C_1$-$C_4$-alkoxy and optionally comprises an N, S or O atom, $R^4$ is a radical from the group of hydrogen; $C_1$-$C_8$-alkyl, $C_3$-$C_8$-alkenyl and $C_3$-$C_8$-alkynyl, optionally mono- to trisubstituted independently of one another by halogen, $C_1$-$C_4$-alkoxy and $C_1$-$C_4$-alkyl-$S(O)_n$—; $C_3$-$C_8$-cycloalkyl and $C_3$-$C_8$-cycloalkyl-$C_1$-$C_4$-alkyl, optionally mono- or disubstituted independently of one another by halogen, $C_1$-$C_4$-alkyl, $C_1$-$C_4$-haloalkyl, $C_1$-$C_4$-alkoxy and cyano; aryl and hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, nitro and cyano; straight-chain or branched aryl-$C_1$-$C_4$-alkyl and hetaryl-$C_1$-$C_4$-alkyl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-$S(O)_n$—, $C_1$-$C_4$-haloalkoxy, $C_1$-$C_4$-haloalkyl-$S(O)_n$—, nitro and cyano, and n is a number 0, 1 or 2 and A, Q, V, W, Y, T and $R^c$ have the definitions according to configuration 2 or configuration 3 or configuration 4 or configuration 5. (Configuration 15)

Furthermore, in the compounds of the formulae (I), (II) and (III), particularly advantageously X is a radical from the group of halogen, $C(O)L^1$, $C(O)OL^1$, $C(O)NL^2L^3$, $C_2$-$C_8$-alkenyl or $C_2$-$C_8$-alkynyl, optionally mono- to pentasubstituted by halogen and mono- or disubstituted by $C_1$-$C_4$-alkoxy, $C_1$-$C_4$-alkyl-S(O)$_n$— and cyano, aryl or hetaryl substituted by aryl or hetaryl, optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, $C_1$-$C_4$-alkylcarboxy, NL$^2$L$^3$, nitro, cyano or optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano; or is an aryl or hetaryl ring which, on two adjacent ring positions, is bonded to a chain consisting of one or two heteroatoms from the group of N, S or O and one or two carbon atoms and this forms in this case a heteroaromatic or optionally partially unsaturated heterocyclic ring, and straight-chain or branched aryl-$C_1$-$C_4$-alkyl or hetaryl-$C_1$-$C_4$-alkyl substituted by aryl or hetaryl optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, $C_1$-$C_4$-alkylcarboxy, NL$^2$L$^3$, nitro, cyano or optionally mono- to trisubstituted independently of one another by halogen, $C_1$-$C_4$-alkyl, $C_1$-$C_4$-haloalkyl, $C_1$-$C_4$-alkoxy, $C_1$-$C_4$-alkyl-S(O)$_n$—, $C_1$-$C_4$-haloalkoxy, $C_1$-$C_4$-haloalkyl-S(O)$_n$—, nitro or cyano, wherein L$^1$ is a radical from the group of $C_1$-$C_6$-alkyl, $C_3$-$C_6$-alkenyl or $C_3$-$C_6$-alkynyl, optionally mono- to pentasubstituted independently of one another by fluorine, chlorine, bromine, methoxy, ethoxy or cyano; and $C_3$-$C_6$-cycloalkyl, optionally mono- or disubstituted independently of one another by fluorine, chlorine, bromine, methyl, ethyl, trifluoromethyl, methoxy, ethoxy or cyano; is phenyl, pyridyl, pyrimidinyl or thienyl, optionally mono- or disubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, difluoromethoxy, trifluoromethoxy, trifluoromethyl-S(O)$_n$—, difluoroethyl-S(O)$_n$—, trifluoroethyl-S(O)$_n$—, nitro or cyano; is straight-chain or branched phenyl-$C_1$-$C_2$-alkyl or pyridyl-$C_1$-$C_2$-alkyl, optionally mono- or disubstituted independently of one another by fluorine, chlorine, bromine, methyl, ethyl, difluoromethyl, trifluoromethyl, methoxy, ethoxy, Me-S(O)$_n$—, Et-S(O)$_n$—, difluoromethoxy, trifluoromethoxy, trifluoromethyl-S(O)$_n$—, difluoroethyl-S(O)$_n$—, trifluoroethyl-S(O)$_n$—, nitro or cyano, L$^2$ is a radical from the group of hydrogen; $C_1$-$C_4$-alkyl, $C_3$-$C_4$-alkenyl or $C_3$-$C_4$-alkynyl, optionally mono- to trisubstituted independently of one another by fluorine or chlorine; $C_3$-$C_6$-cycloalkyl, optionally mono- or disubstituted independently of one another by fluorine, chlorine, methyl, ethyl, trifluoromethyl, methoxy, ethoxy or cyano; or is $C_1$-$C_4$-alkylcarbonyl or $C_1$-$C_4$-alkoxycarbonyl, optionally mono- to trisubstituted independently of one another by fluorine, chlorine, methoxy or ethoxy; and is phenyl-$C_1$-$C_2$-alkoxycarbonyl, optionally mono- or disubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, difluoromethoxy, trifluoromethoxy, trifluoromethyl-S(O)$_n$—, difluoroethyl-S(O)$_n$—, trifluoroethyl-S(O)$_n$—, nitro or cyano, L$^3$ is a radical from the group of hydrogen; $C_1$-$C_4$-alkyl, $C_3$-$C_6$-alkenyl, $C_3$-$C_6$-alkynyl or $C_1$-$C_4$-alkoxy, optionally mono- to trisubstituted independently of one another by halogen, methoxy, ethoxy, n- or isopropoxy or methyl-S(O)$_n$—; $C_3$-$C_6$-cycloalkyl or $C_3$-$C_6$-cycloalkyl-$C_1$-$C_4$-alkyl, optionally mono- or disubstituted independently of one another by fluorine, chlorine, methyl, ethyl, trifluoromethyl, methoxy, ethoxy or cyano; phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl or thiadiazolyl, optionally mono- or disubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, difluoromethoxy, trifluoromethoxy, trifluoromethyl-S(O)$_n$—, difluoroethyl-S(O)$_n$—, trifluoroethyl-S(O)$_n$—, nitro or cyano; straight-chain or branched phenyl-$C_1$-$C_2$-alkyl or pyridyl-$C_1$-$C_2$-alkyl, optionally mono- or disubstituted independently of one another by fluorine, chlorine, bromine, methyl, ethyl, difluoromethyl, trifluoromethyl, methoxy, ethoxy, Me-S(O)$_n$—, Et-S(O)$_n$—, difluoromethoxy, trifluoromethoxy, trifluoromethyl-S(O)$_n$—, difluoroethyl-S(O)$_n$—, trifluoroethyl-S(O)$_n$—, nitro or cyano, or L$^2$ and L$^3$ together form a four- to six-membered aliphatic ring which optionally comprises an N, S or O atom and is optionally mono- or disubstituted by fluorine, chlorine, bromine, methyl, ethyl, methoxy or ethoxy and n is a number 0, 1 or 2 and A, Q, V, W, Y, T and R$^c$ have the definitions according to configuration 1 or configuration 3 or configuration 4 or configuration 5. (Configuration 16)

Furthermore, in the compounds of the formulae (I), (II) and (III), particularly advantageously X is a radical from the group of halogen, C(O)L$^1$, C(O)OL$^1$, C(O)NL$^2$L$^3$, vinyl, allyl, methallyl, 2-butenyl, propargyl, ethynyl and 2-butynyl, optionally mono- to trisubstituted independently of one another by fluorine, chlorine and bromine and/or monosubstituted by methoxy, ethoxy, methylsulfanyl, ethylsulfanyl, methylsulfinyl, ethylsulfinyl, methylsulfonyl, ethylsulfonyl or cyano, aryl or hetaryl substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano or is an aryl or hetaryl ring which, on two adjacent ring positions, is bonded to a chain consisting of one or two oxygen atoms and one or two carbon atoms and this forms in this case a heteroaromatic or optionally partially unsaturated heterocyclic ring, and straight-chain or branched aryl-$C_1$-$C_4$-alkyl or hetaryl-$C_1$-$C_4$-alkyl substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, cyclopropylmethyl-$S(O)_n$—, difluoromethoxy, trifluoromethoxy, trifluoromethyl-$S(O)_n$—, difluoroethyl-$S(O)_n$—, trifluoroethyl-$S(O)_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, cyclopropylmethyl-$S(O)_n$—, difluoromethoxy, trifluoromethoxy, trifluoromethyl-$S(O)_n$—, difluoroethyl-$S(O)_n$—, trifluoroethyl-$S(O)_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano, wherein $L^1$ is a radical from the group of $C_1$-$C_6$-alkyl, optionally mono- to pentasubstituted independently of one another by fluorine, chlorine, bromine, methoxy, ethoxy or cyano; phenylmethyl, optionally mono- or disubstituted independently of one another by fluorine, chlorine, bromine, methyl, ethyl, difluoromethyl, trifluoromethyl, methoxy, ethoxy, Me-$S(O)_n$—, Et-$S(O)_n$—, difluoromethoxy, trifluoromethoxy, trifluoromethyl-$S(O)_n$—, difluoroethyl-$S(O)_n$—, trifluoroethyl-$S(O)_n$—, nitro or cyano, or is $C_3$-$C_6$-cycloalkyl, $L^2$ is a radical from the group of hydrogen; $C_1$-$C_4$-alkyl, $C_1$-$C_4$-alkylsulfonyl, $C_3$-$C_6$-cycloalkylsulfonyl, $C_1$-$C_4$-alkylcarbonyl or $C_1$-$C_4$-alkoxycarbonyl, optionally mono- to trisubstituted independently of one another by fluorine, chlorine, methoxy or ethoxy; and arylmethoxycarbonyl, optionally mono- to trisubstituted independently of one another by fluorine, chlorine, bromine, methyl, ethyl, trifluoromethyl, methoxy or ethoxy, $L^3$ is a radical from the group of hydrogen; $C_1$-$C_4$-alkyl, $C_3$-$C_6$-alkenyl, $C_3$-$C_6$-alkynyl or $C_1$-$C_4$-alkoxy, optionally mono- to trisubstituted independently of one another by halogen, hydroxyl, methoxy, ethoxy, methoxycarbonyl, ethoxycarbonyl or cyano; $C_3$-$C_6$-cycloalkyl or $C_3$-$C_6$-cycloalkyl-$C_1$-$C_4$-alkyl, optionally mono- or disubstituted independently of one another by fluorine, chlorine, methyl, ethyl, trifluoromethyl, methoxy, ethoxy or cyano; phenyl, pyridyl or thienyl, optionally mono- or disubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, trifluoromethoxy, nitro or cyano; phenyl-$C_1$-$C_2$-alkyl or pyridyl-$C_1$-$C_2$-alkyl, optionally mono- or disubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, trifluoromethoxy, nitro or cyano, or $L^2$ and $L^3$ together form a four- to six-membered aliphatic ring which optionally comprises an N, S or O atom and is optionally mono- or disubstituted by fluorine, chlorine, bromine, methyl, ethyl, methoxy or ethoxy and n is a number 0, 1 or 2 and A, Q, V, W, Y, T and $R^c$ have the definitions according to configuration 1 or configuration 2 or configuration 4 or configuration 5. (Configuration 17)

Furthermore, in the compounds of the formulae (I), (II) and (III), particularly advantageously X is a radical from the group of halogen, $C(O)L^1$, $C(O)OL^1$, $C(O)NL^2L^3$, vinyl, allyl, methallyl, 2-butenyl, propargyl, ethynyl and 2-butynyl, optionally mono- to trisubstituted independently of one another by fluorine, chlorine and bromine and/or monosubstituted by methoxy, ethoxy, methylsulfanyl, ethylsulfanyl, methylsulfinyl, ethylsulfinyl, methylsulfonyl, ethylsulfonyl or cyano, phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, cyclopropylmethyl-$S(O)_n$—, difluoromethoxy, trifluoromethoxy, trifluoromethyl-$S(O)_n$—, difluoroethyl-$S(O)_n$—, trifluoroethyl-$S(O)_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, cyclopropylmethyl-$S(O)_n$—, difluoromethoxy, trifluoromethoxy, trifluoromethyl-$S(O)_n$—, difluoroethyl-$S(O)_n$—, trifluoroethyl-$S(O)_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano or is a phenyl which, on two adjacent ring positions, is bonded to a chain consisting of one or two oxygen atoms and one or two carbon atoms and this forms in this case an optionally partially unsaturated heterocyclic ring and straight-chain or branched phenyl-$C_1$-$C_2$-alkyl, pyridyl-$C_1$-$C_2$-alkyl, pyrimidyl-$C_1$-$C_2$-alkyl, thiazolyl-$C_1$-$C_2$-alkyl and pyrazolyl-$C_1$-$C_2$-alkyl substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-$S(O)_n$—, ethyl-$S(O)_n$—, cyclopropylmethyl-$S(O)_n$—, difluoromethoxy, trifluoromethoxy, trifluoromethyl-$S(O)_n$—, difluoroethyl-$S(O)_n$—, trifluoroethyl-$S(O)_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano, wherein $L^1$ is a radical from the group of methyl, ethyl, n- or isopropyl, 1-cyano-1-methylethyl or cyclopropyl, $L^2$ is a radical from the group of hydrogen, methyl, ethyl, methylsulfonyl, cyclopropylsulfonyl, methoxycarbonyl, ethoxycarbonyl, 2-methoxyethoxycarbonyl n-, iso, sec- or t-butoxycarbonyl, $L^3$ is a radical from the group of hydrogen, methyl, ethyl, n- or isopropyl, n-, iso, sec- or tert-butyl, 2,2,2-trifluoroethyl, 2-hydroxyethyl, 2-methoxyethyl, cyanomethyl, methoxycarbonylmethyl, ethoxycarbonylmethyl, cyclopropyl, 1-cyanocyclopropyl, cyclopropylmethyl, cyclobutyl, cyclopentyl, cyclohexyl, methoxy, ethoxy, phenyl, 2-C$_1$-phenyl, 3-Cl-phenyl, 4-Cl-phenyl, pyridyl, phenylmethyl, 1-phenyl-2-hydroxyethyl, 2-C$_1$-phenylmethyl, 3-Cl-phenylmethyl, 4-Cl-phenylmethyl, or $L^2$ and $L^3$ together are (CH$_2$)$_5$, (CH$_2$)$_4$, (CH$_2$)$_3$ or (CH$_2$)$_2$O (CH$_2$)$_2$, and n is a number 0, 1 or 2 and A, Q, V, W, Y, T and R$^c$ have the definitions according to configuration 1 or configuration 2 or configuration 3. (Configuration 18)

Advantageously, the substituted imidazolyl carboxyamides of the formula (II) can be prepared by the method according to the invention with good yields and in high purity. Because of the very good functional group tolerance of zinc reagents, zinc bases are very attractive. Regio- and chemoselective metallations of imidazolyl carboxyamides in the presence of stoichiometric amounts of selective bases are made possible, even at elevated temperatures, without decomposition of the imidazolyl skeleton taking place or sensitive functional groups being attacked. The zinc compound formed as intermediate can subsequently be scavenged with various electrophiles, as described by way of example in Organic Letters 2009 (11), p. 1837ff. These imidazopyridine derivatives having novel substitution can then be further reacted as valuable synthons.

Especially advantageous is furthermore the possibility of being able to conduct Negishi couplings even at distinctly lower temperatures, in which case even functional groups that are sensitive at higher temperatures, such as amides, esters or fluorine atoms, are tolerated in methods according to the invention without impairing the regioselectivity that exists. Moreover, Negishi cross-couplings within the context of a method according to the invention can also give rise to good yields of target product in the presence of, for example, ortho substituents on the pyridine skeleton, even though such couplings with 2-substituted pyridine derivatives have to date been known for giving very low yields. Thus, further and/or more flexible derivatizations of reactant and product are possible without having to constantly alter or adapt synthesis routes.

The method according to the invention can be elucidated by way of example by the following scheme (I):

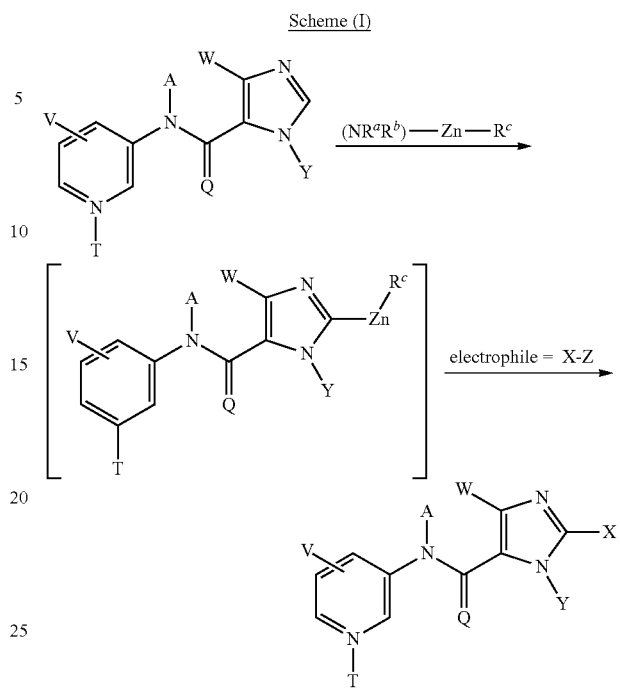

Scheme (I)

Q, A, V, T, W, Y, X, Z and R$^c$ herein have the definitions specified hereinabove. The compounds shown in brackets are the intermediate (formula (IIIa)) which is reacted further to give the compound of the formula (II). Accordingly, the method according to the invention can be divided into the two method steps a) and b), step a) being the conversion of the compound of the formula (I) to the respective intermediate and step b) being the further conversion of the intermediate to the compound of the formula (II).

GENERAL DEFINITIONS

In the context of the present invention, the term halogen, unless defined otherwise, encompasses those elements selected from the group consisting of fluorine, chlorine, bromine and iodine.

The term "halides" in connection with the present invention describes compounds between halogens and elements of other groups of the Periodic Table, where halide salts (ionic compounds (salts)) which consist of anions and cations because of the great difference in electronegativity between the elements involved and are held together by electrostatic interactions) or covalent halides (covalent compounds where the difference in electronegativity is not as great as in the aforementioned ionic compounds, but the bonds have charge polarity) may be present, depending on the nature of the chemical bond. Particular preference is given in accordance with the invention to halide salts.

The term "pivaloyl" in the context of the present invention describes the deprotonated radical of pivalic acid (IX) having the empirical formula (CH$_3$)$_3$CCO$_2$H.

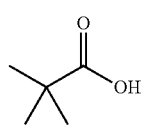

(IX)

"O-pivaloyl" correspondingly means that the bond of the pivaloyl radical is via the deprotonated oxygen atom of the acid group.

Optionally substituted groups can be mono- or polysubstituted, it being possible for the substituents in the case of polysubstitutions to be identical or different.

In the context of the present invention, unless defined differently elsewhere, the term "alkyl", either on its own or else in combination with further terms, for example haloalkyl, is understood to mean a radical of a saturated, aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl.

The term "alkoxy", either on its own or else in combination with further terms, for example haloalkoxy, is understood in the present case to mean an O-alkyl radical, where the term "alkyl" is as defined above.

Halogen-substituted radicals are mono- or polyhalogenated, up to the maximum number of possible substituents. In the case of polyhalogenation, the halogen atoms may be identical or different.

According to the invention, unless defined differently elsewhere, the term "aryl" is understood to mean an aromatic radical having 6 to 14 carbon atoms, preferably phenyl, naphthyl, anthryl or phenanthrenyl, more preferably phenyl.

Unless defined differently elsewhere, the term "arylalkyl" is understood to mean a combination of the radicals "aryl" and "alkyl" defined according to the invention, where the radical is generally attached via the alkyl group. Examples of these are benzyl, phenylethyl or α-methylbenzyl, benzyl being particularly preferred.

Unless defined differently elsewhere, "hetaryl" denotes a mono-, bi- or tricyclic heterocyclic group of carbon atoms and at least one heteroatom, where at least one cycle is aromatic. Preferably, the hetaryl group contains 3, 4, 5, 6, 7 or 8 carbon atoms and is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl, imidazopyridinyl and indolizinyl.

Unless stated otherwise, optionally substituted radicals may be mono- or polysubstituted, where the substituents in the case of polysubstitutions may be the same or different.

The conversion of the compounds of the formula (I) to compounds of the formula (III) in the first method step (step a)) is effected in the presence of an organozinc base of the structure $(NR^aR^b)$—Zn—$R^c$ or $(NR^aR^b)_2$—Zn, in which (configuration B-1)

$R^c$ is as defined above (configuration 1) (and is therefore halogen or —O-pivaloyl), $R^a$ and $R^b$ together form a —$(CH_2)_4$—, —$(CH_2)_5$— or —$(CH_2)_2O(CH_2)_2$— group, where each of these groups may optionally be substituted by 1, 2, 3 or 4 $R^d$ radicals and $R^d$ is selected from the group consisting of methyl, ethyl, n-propyl and isopropyl.

It is preferable that (configuration B-2)

$R^c$ is as defined above as preferred (configuration 2) (and is therefore —O-pivaloyl, chlorine, bromine or iodine), $R^a$ and $R^b$ together form a —$(CH_2)_5$— group, where each of these groups may optionally be substituted by 1, 2, 3 or 4 $R^d$ radicals and $R^d$ is selected from the group consisting of methyl and ethyl.

It is particularly preferable that (configuration B-3)

$R^c$ is as defined above as emphasized (configuration 5) (and is therefore bromine or chlorine, preferably chlorine) and $R^a$ and $R^b$ together form a —$(CH_2)_5$— group substituted by 4 methyl groups.

The radical definitions given above can be combined with one another as desired, i.e. including combinations between the respective preferred ranges.

In a very particularly preferred configuration of the base according to the invention, the structural element $(NR^aR^b)$ is tetramethylpiperidine (TMP) of formula (V).

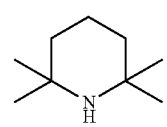

(V)

Organozinc bases very particularly preferred in accordance with the invention are accordingly characterized in that zinc is bound to TMP, especially in the form of zinc halide and most preferably in the form of zinc chloride. Bases of this kind have the following structure of the formula (VI) (configuration B-4)

$$(TMP)_xZnCl_{2-x}, \quad (VI)$$

in which x is the number 1 or 2. Among these, preference is given in turn to bases where x=1 (configuration B-5) according to formula (VII):

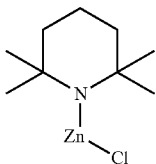

(VII)

In a further preferred embodiment of the method according to the invention, the organometallic base is present in conjunction with alkali metal halides or alkaline earth metal halides. This is especially true of bases of the formulae (VI) and (VII). Particularly preferred alkali metal halides or alkaline earth metal halides of this kind are lithium chloride and magnesium chloride, very particular preference being given to lithium chloride. Organometallic bases that are very particularly preferred in accordance with the invention are accordingly TMP ZnCl.LiCl or (TMP)$_2$ Zn.2LiCl or (TMP)$_2$ Zn.2LiCl 2 MgCl$_2$ (configuration B-6). Most preferred is TMP ZnCl.LiCl (VIII; configuration B-7).

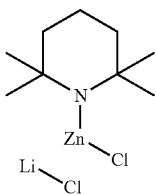

(VIII)

Specific combinations of compounds of the formulae (I), (II) and (III) with bases according to the invention are cited by way of example in Table 1, hereinafter these being employable in a method according to the invention. Since, in some configurations, the structural element $R^c$ is present both in the base according to the invention and in the compound of the formula (III), the narrowest definition applies to $R^c$ in each case.

TABLE 1

| Number | Compounds of the formulae (I), (II) and (III) | Base according to |
|---|---|---|
| 1 | Configuration 1 | Configuration B-1 |
| 2 | Configuration 1 | Configuration B-2 |
| 3 | Configuration 1 | Configuration B-3 |
| 4 | Configuration 1 | Configuration B-4 |
| 5 | Configuration 1 | Configuration B-5 |
| 6 | Configuration 1 | Configuration B-6 |
| 7 | Configuration 1 | Configuration B-7 |
| 8 | Configuration 2 | Configuration B-1 |
| 9 | Configuration 2 | Configuration B-2 |
| 10 | Configuration 2 | Configuration B-3 |
| 11 | Configuration 2 | Configuration B-4 |
| 12 | Configuration 2 | Configuration B-5 |
| 13 | Configuration 2 | Configuration B-6 |
| 14 | Configuration 2 | Configuration B-7 |
| 15 | Configuration 3 | Configuration B-1 |
| 16 | Configuration 3 | Configuration B-2 |
| 17 | Configuration 3 | Configuration B-3 |
| 18 | Configuration 3 | Configuration B-4 |
| 19 | Configuration 3 | Configuration B-5 |
| 20 | Configuration 3 | Configuration B-6 |
| 21 | Configuration 3 | Configuration B-7 |
| 22 | Configuration 4 | Configuration B-1 |
| 23 | Configuration 4 | Configuration B-2 |

TABLE 1-continued

| Number | Compounds of the formulae (I), (II) and (III) | Base according to |
|---|---|---|
| 24 | Configuration 4 | Configuration B-3 |
| 25 | Configuration 4 | Configuration B-4 |
| 26 | Configuration 4 | Configuration B-5 |
| 27 | Configuration 4 | Configuration B-6 |
| 28 | Configuration 4 | Configuration B-7 |
| 29 | Configuration 5 | Configuration B-1 |
| 30 | Configuration 5 | Configuration B-2 |
| 31 | Configuration 5 | Configuration B-3 |
| 32 | Configuration 5 | Configuration B-4 |
| 33 | Configuration 5 | Configuration B-5 |
| 34 | Configuration 5 | Configuration B-6 |
| 35 | Configuration 5 | Configuration B-7 |
| 36 | Configuration 6 | Configuration B-1 |
| 37 | Configuration 6 | Configuration B-2 |
| 38 | Configuration 6 | Configuration B-3 |
| 39 | Configuration 6 | Configuration B-4 |
| 40 | Configuration 6 | Configuration B-5 |
| 41 | Configuration 6 | Configuration B-6 |
| 42 | Configuration 6 | Configuration B-7 |
| 43 | Configuration 7 | Configuration B-1 |
| 44 | Configuration 7 | Configuration B-2 |
| 45 | Configuration 7 | Configuration B-3 |
| 476 | Configuration 7 | Configuration B-4 |
| 48 | Configuration 7 | Configuration B-5 |
| 49 | Configuration 7 | Configuration B-6 |
| 50 | Configuration 7 | Configuration B-7 |
| 51 | Configuration 8 | Configuration B-1 |
| 51 | Configuration 8 | Configuration B-2 |
| 51 | Configuration 8 | Configuration B-3 |
| 54 | Configuration 8 | Configuration B-4 |
| 55 | Configuration 8 | Configuration B-5 |
| 56 | Configuration 8 | Configuration B-6 |
| 57 | Configuration 8 | Configuration B-7 |
| 58 | Configuration 9 | Configuration B-1 |
| 59 | Configuration 9 | Configuration B-2 |
| 60 | Configuration 9 | Configuration B-3 |
| 61 | Configuration 9 | Configuration B-4 |
| 62 | Configuration 9 | Configuration B-5 |
| 63 | Configuration 9 | Configuration B-6 |
| 64 | Configuration 9 | Configuration B-7 |
| 65 | Configuration 10 | Configuration B-1 |
| 66 | Configuration 10 | Configuration B-2 |
| 67 | Configuration 10 | Configuration B-3 |
| 68 | Configuration 10 | Configuration B-4 |
| 69 | Configuration 10 | Configuration B-5 |
| 70 | Configuration 10 | Configuration B-6 |
| 71 | Configuration 10 | Configuration B-7 |
| 72 | Configuration 11 | Configuration B-1 |
| 73 | Configuration 11 | Configuration B-2 |
| 74 | Configuration 11 | Configuration B-3 |
| 75 | Configuration 11 | Configuration B-4 |
| 76 | Configuration 11 | Configuration B-5 |
| 77 | Configuration 11 | Configuration B-6 |
| 78 | Configuration 11 | Configuration B-7 |
| 79 | Configuration 12 | Configuration B-1 |
| 80 | Configuration 12 | Configuration B-2 |
| 81 | Configuration 12 | Configuration B-3 |
| 82 | Configuration 12 | Configuration B-4 |
| 83 | Configuration 12 | Configuration B-5 |
| 84 | Configuration 12 | Configuration B-6 |
| 85 | Configuration 12 | Configuration B-7 |
| 86 | Configuration 13 | Configuration B-1 |
| 87 | Configuration 13 | Configuration B-2 |
| 88 | Configuration 13 | Configuration B-3 |
| 89 | Configuration 13 | Configuration B-4 |
| 90 | Configuration 13 | Configuration B-5 |
| 91 | Configuration 13 | Configuration B-6 |
| 92 | Configuration 13 | Configuration B-7 |
| 93 | Configuration 14 | Configuration B-1 |
| 94 | Configuration 14 | Configuration B-2 |
| 95 | Configuration 14 | Configuration B-3 |
| 96 | Configuration 14 | Configuration B-4 |
| 97 | Configuration 14 | Configuration B-5 |
| 98 | Configuration 14 | Configuration B-6 |
| 99 | Configuration 14 | Configuration B-7 |
| 100 | Configuration 15 | Configuration B-1 |

TABLE 1-continued

| Number | Compounds of the formulae (I), (II) and (III) | Base according to |
|---|---|---|
| 101 | Configuration 15 | Configuration B-2 |
| 102 | Configuration 15 | Configuration B-3 |
| 103 | Configuration 15 | Configuration B-4 |
| 104 | Configuration 15 | Configuration B-5 |
| 105 | Configuration 15 | Configuration B-6 |
| 106 | Configuration 15 | Configuration B-7 |
| 107 | Configuration 16 | Configuration B-1 |
| 108 | Configuration 16 | Configuration B-2 |
| 109 | Configuration 16 | Configuration B-3 |
| 110 | Configuration 16 | Configuration B-4 |
| 111 | Configuration 16 | Configuration B-5 |
| 112 | Configuration 16 | Configuration B-6 |
| 113 | Configuration 16 | Configuration B-7 |
| 114 | Configuration 17 | Configuration B-1 |
| 115 | Configuration 17 | Configuration B-2 |
| 116 | Configuration 17 | Configuration B-3 |
| 117 | Configuration 17 | Configuration B-4 |
| 118 | Configuration 17 | Configuration B-5 |
| 119 | Configuration 17 | Configuration B-6 |
| 120 | Configuration 17 | Configuration B-7 |
| 121 | Configuration 18 | Configuration B-1 |
| 122 | Configuration 18 | Configuration B-2 |
| 123 | Configuration 18 | Configuration B-3 |
| 124 | Configuration 18 | Configuration B-4 |
| 125 | Configuration 18 | Configuration B-5 |
| 126 | Configuration 18 | Configuration B-6 |
| 127 | Configuration 18 | Configuration B-7 |

Preferably, the organozinc base is used in the method according to the invention in a total amount of 0.5 to 5 equivalents, preferably of 0.8 to 2 equivalents, further preferably of 1 to 1.5 equivalents and more preferably of 1.0 to 1.2 equivalents, based on the compound of the formula (I). One advantage of the method according to the invention in this regard is that the organometallic base can be used in virtually stoichiometric amounts.

The conversion of the compounds of the formula (III) to compounds of the formula (II) in the second method step (step b)) takes place in the presence of a compound X—Z, in which X has the definition according to any of configurations 1 to 5 and Z is preferably chlorine, bromine, iodine or fluorine (configuration (C-1)), particularly preferably bromine or iodine (C-2) and especially preferably iodine (C-3).

Listed by way of example in Table 2 below are compounds X—Z which may be used in a method according to the invention.

TABLE 2

| Number | X | Z |
|---|---|---|
| 1 | Configuration 1 | Configuration C-1 |
| 2 | Configuration 1 | Configuration C-2 |
| 3 | Configuration 1 | Configuration C-3 |
| 4 | Configuration 2 | Configuration C-1 |
| 5 | Configuration 2 | Configuration C-2 |
| 6 | Configuration 2 | Configuration C-3 |
| 7 | Configuration 3 | Configuration C-1 |
| 8 | Configuration 3 | Configuration C-2 |
| 9 | Configuration 3 | Configuration C-3 |
| 10 | Configuration 4 | Configuration C-1 |
| 11 | Configuration 4 | Configuration C-2 |
| 12 | Configuration 4 | Configuration C-3 |
| 13 | Configuration 5 | Configuration C-1 |
| 14 | Configuration 5 | Configuration C-2 |
| 15 | Configuration 5 | Configuration C-3 |

Preferably, the compound X—Z is used in the method according to the invention in a total amount of 0.5 to 10.0 equivalents, preferably of 0.8 to 5 equivalents, further preferably of 1 to 2.5 equivalents and more preferably of 1.0 to 2.0 equivalents, based on the compound of the formula (I).

The conversion according to the invention of the compounds of the formula (I) to compounds of the formula (III) and further to compounds of the formula (II) is preferably effected in the presence of an organic solvent in each case. Useful solvents in principle include all organic solvents which are inert under the reaction conditions employed and in which the compounds to be converted have adequate solubility. Suitable solvents especially include: tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, ethylene carbonate, propylene carbonate, N,N-dimethylacetamide, N,N-dimethylformamide (DMF), N-methylpyrrolidone (NMP), N-ethyl-2-pyrrolidone (NEP), N-butyl-2-pyrrolidone (NBP); N,N'-dimethylpropyleneurea (DMPU), halohydrocarbons and aromatic hydrocarbons, especially chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, especially 1,2-dichlorobenzene, chlorotoluene, trichlorobenzene; 4-methoxybenzene, fluorinated aliphatics and aromatics, such as trichlorotrifluoroethane, benzotrifluoride and 4-chlorobenzotrifluoride. It is also possible to use solvent mixtures, preferably mixtures of the solvents mentioned above such as tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, dimethylformamide (DMF).

Preferred solvents are THF, N,N-dimethylformamide (DMF), 1,4-dioxane, diglyme, methyl tert-butyl ether (MTBE), tert-amyl methyl ether (TAME), 2-methyl-THF, toluene and 4-methoxybenzene.

Particularly preferred solvents are THF and N,N-dimethylformamide (DMF), very particular preference being given to THF.

The solvent may also be degassed (oxygen-free).

Preference is given to using the same solvent for both method steps a) and b). Alternative configurations of the invention in which different solvents are used for method steps a) and b) are likewise possible, however, in which case the solvents are then likewise preferably selected from the aforementioned solvents, and the respective solvents specified as being preferred, particularly preferred and especially preferred are applicable to the respective method step a) or b).

The conversion in method step a) is generally conducted at a temperature between 0° C. and 80° C. and with increasing preference between 10° C. and 70° C., between 15° C. and 60° C., between 20° C. and 50° C., between 20° C. and 40° C., and most preferably between 20° C. and 35° C., for example at room temperature or 25° C.

The conversion in method step a) generally takes place over a period of 10 to 90 minutes, preferably 15 to 60 minutes and particularly preferably 20 to 45 minutes, for example 30 minutes.

The compounds of the formula (III) represent versatile usable intermediate compounds by which, via different reactions in method step b), a multiplicity of substituents X may be introduced directly by reaction with compounds of the formula X—Z.

The conversion of the compounds of the formula (III) to compounds of the formula (III) (step b), i.e. the introduction of the radical X, is preferably carried out by coupling, particularly preferably by a cross-coupling or by nucleophilic substitution.

Conversions of this kind are described, for example, in Organic Letters 2008 (10), p. 2497ff or Angewandte Chemie International Edition 2013 (53), p. 1430ff.

The conversion in method step b) is generally conducted at a temperature between −40° C. and 120° C. and with increasing preference between −35° C. and 100° C. and especially preferably between −30° C. and 90° C.

The conversion in method step b) generally takes place over a period of 5 minutes to 12 h, preferably 10 minutes to 10 h and particularly preferably 20 minutes to 2 h.

The reaction is typically conducted at standard pressure, but can also be conducted at elevated or reduced pressure.

The desired compounds of the formula (II) can be isolated, for example, by aqueous workup in the presence of saturated ammonium chloride or sodium thiosulfate solutions and/or subsequent chromatography. Such methods are known to those skilled in the art and also include crystallization from an organic solvent or solvent mixture.

Introduction of the Radical X Via Cross-Coupling:

The compounds of the formula (II) can be prepared by cross-couplings, in particular by Negishi cross-coupling of the compounds of the formula (III) with the compounds X—Z in the presence of a catalyst such as described, for example, in Angewandte Chemie International Edition 2013 (53), p. 1430ff.

Preference is given to using compounds as X—Z in this case in which X has the definition according to any of configurations 1 to 5, but is not halogen, and Z has the definitions stated above, in particular according to any of configurations C-1 to C-3.

In this case, the compound X—Z is preferably used in the method according to the invention in a total amount of 0.5 to 10.0 equivalents, preferably of 0.8 to 5 equivalents, further preferably of 1 to 2.5 equivalents and more preferably of 1.0 to 2.0 equivalents, based on the compound of the formula (I).

The cross-coupling is further effected in the presence of a catalyst. Preferably, the catalyst is a palladium compound or a nickel compound. More preferably, the catalyst is a palladium compound. It is especially preferably tetrakis(triphenylphosphine)palladium(0), abbreviated to Pd(PPh$_3$)$_4$.

Typically, 2.5 to 25 mol % and preferably 5 to 20 mol % of catalyst, particularly tetrakis(triphenylphosphine)palladium(0), are used.

The cross-coupling is generally conducted at a temperature between 0° C. and 120° C. and with increasing preference between 10° C. and 100° C. and especially preferably between 25° C. and 90° C.

The cross-coupling generally takes place over a period of 5 minutes to 12 h, preferably 15 minutes to 10 h and particularly preferably 30 minutes to 2 h.

Introduction of the Radical X Via Nucleophilic Substitution:

The compounds of the formula (II) can be prepared by copper-catalysed reactions of the compounds of the formula (III) with the compounds X—Z such as described, for example, in Organic Letters 2008 (10), p. 2497ff.

Preference is given to using compounds as X—Z in this case in which X is halogen, and Z has the definitions stated above, in particular according to any of configurations C-1 to C-3. The compound X—Z, as apparent from the definitions of X and Z, is therefore an interhalogen compound, preferably elemental halogen. X and Z need not necessarily be the same halogen. For example, X may be iodine or bromine and Z may be chlorine, bromine or iodine. Preferably, the compound X—Z, however, is elemental halogen, in particular F$_2$, Cl$_2$, Br$_2$ or I$_2$. Particular preference is given to I$_2$ or Br$_2$, very particular preference to I$_2$.

In this case, the compound X—Z is preferably used in the method according to the invention in a total amount of 0.5 to 10.0 equivalents, preferably of 0.8 to 5 equivalents, further preferably of 1 to 2.5 equivalents and more preferably of 1.0 to 2.0 equivalents, based on the compound of the formula (I).

The reaction is generally conducted at a temperature between −10° C. and 70° C. and with increasing preference between −5° C. and 50° C. and especially preferably between 10° C. and 25° C.

The reaction generally takes place over a period of 5 to 60 minutes, preferably 15 to 45 minutes and particularly preferably 20 to 40 minutes.

The preparation of the compounds of the formula (I) is described, for example, in WO2016/128298 (page 24, method D).

The present invention further provides compounds of the formula (IIIa) or (IIIb)

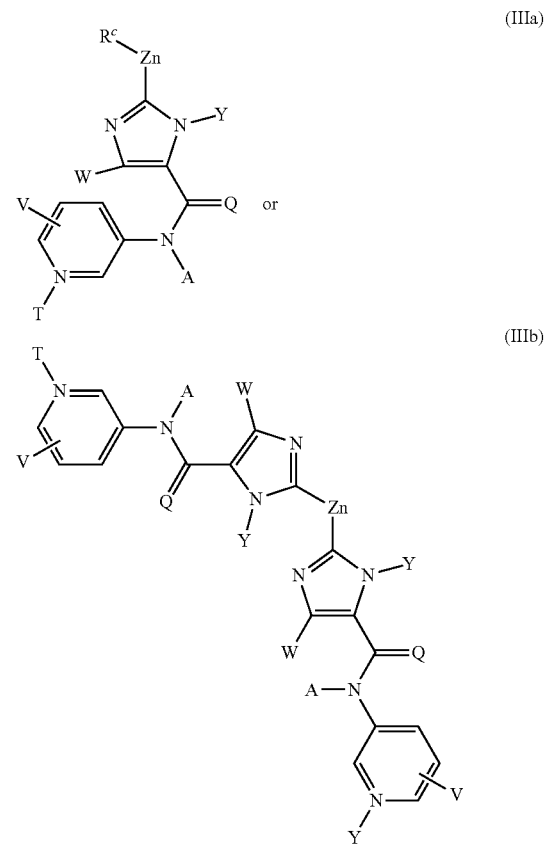

in which Q, A, V, T, W, Y and R$^c$ have the definitions stated above and preferred configurations according to any of configurations 1 to 14.

The compounds of the formula (IIIa) or (IIIb) may also be present complexed with salts, wherein the salts are preferably alkali metal halides or alkaline earth metal halides, preferably lithium chloride and/or magnesium chloride and particularly preferably lithium chloride.

The compounds of the formulae (IIIa) and (IIIb) moreover may also be present as salts themselves.

The compounds of the formula (IIIa) and (IIIb) represent versatile and therefore very valuable synthons, for example for preparing compounds of the formula (II).

Among the compounds of the formula (IIIa), the following compounds are especially preferred, in which the respective compound can be present alone or as a lithium chloride complex:

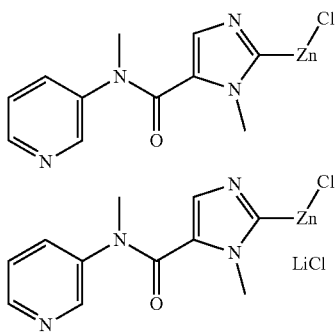

chloro {1-methyl-5-[methyl(pyridin-3-yl)carbamoyl]-1H-imidazol-2-yl}zinc chloro{1-methyl-5-[methyl(pyridin-3-yl)carbamoyl]-1H-imidazol-2-yl}zinc lithium chloride complex The present invention is elucidated in more detail by the examples which follow, although the examples should not be interpreted in a manner that restricts the invention.

Methods:

The log P values are measured according to EEC Directive 79/831 Annex V.A8 by HPLC (high-performance liquid chromatography) on a reversed-phase column (C 18). Temperature: 55° C.

The LC-MS determination in the acidic range is carried out at pH 2.7 using the mobile phases 0.1% aqueous formic acid and acetonitrile (contains 0.1% formic acid); linear gradient from 10% acetonitrile to 95% acetonitrile.

The LC-MS determination in the neutral range is carried out at pH 7.8 using the mobile phases 0.001 molar aqueous ammonium bicarbonate solution and acetonitrile; linear gradient from 10% acetonitrile to 95% acetonitrile.

Calibration is carried out using unbranched alkan-2-ones (having 3 to 16 carbon atoms) with known log P values (log P values determined on the basis of the retention times by linear interpolation between two successive alkanones).

The NMR data of selected examples are stated in classic form (δ values, multiplet splitting, number of hydrogen atoms).

In each case, the solvent in which the NMR spectrum was recorded is stated.

EXAMPLE 1

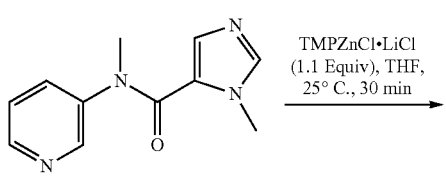

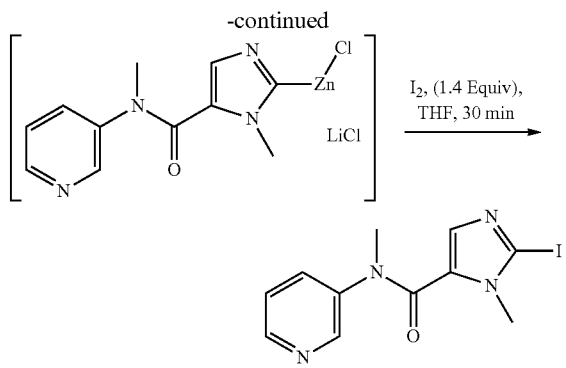

Synthesis of 2-iodo-N,1-dimethyl-N-(pyridin-3-yl)-1H-imidazole-5-carboxamide

To N,1-dimethyl-N-(pyridin-3-yl)-1H-imidazole-5-carboxamide (216 mg, 1.0 mmol), dissolved in THF (2 ml), was added TMPZnCl.LiCl (1.31M in THF, 0.84 ml, 1.1 mmol) at 25° C. under argon; this reaction solution was stirred for 30 minutes. Subsequently, iodine (355 mg) in THF (4 ml) is added at 25° C. and the solution is stirred for a further 30 min. After customary workup by addition of saturated ammonium chloride and sodium thiosulfate solutions, the reaction mixture is extracted with ethyl acetate, and the combined organic phases are dried over Na$_2$SO$_4$ and concentrated in a membrane pump vacuum. After purification by column chromatography (ethyl acetate/cyclohexane), 2-iodo-N, 1-dimethyl-N-(pyridin-3-yl)-1H-imidazole-5-carboxamide (262 mg, 77%) is obtained as a yellow solid.

MH$^+$: 343.0; $^1$H-NMR (d$_6$-DMSO): δ 8.48 (m, 2H), 7.83 (m, 1H), 7.44 (m, 1H), 6.27 (s, 1H), 3.73 (s, 3H), 3.37 (s, 3H).

EXAMPLE 2

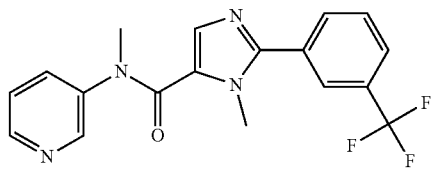 [SMILES: CN(C(=O)c1cnc(-c2cccc(C(F)(F)F)c2)n1C)c1cccnc1]

Synthesis of N,1-dimethyl-N-(pyridin-3-yl)-2-[3-(trifluoromethyl)phenyl]-1H-imidazole-5-carboxamide To N,1-dimethyl-N-(pyridin-3-yl)-1H-imidazole-5-carboxamide (216 mg, 1.0 mmol), dissolved in THF (2 ml), was added TMPZnCl.LiCl (1.31M in THF, 0.84 ml, 1.1 mmol) at 25° C. under argon; this reaction solution was stirred for 30 minutes. Subsequently, 1-iodo-3-(trifluoromethyl)benzene (544 mg, 2 mmol) in THF (3 ml) and tetrakis(triphenylphosphine)palladium(0) (115 mg, 0.1 mmol) were added at 25° C. and the solution was stirred at 80° C. for a further 1 hour. After customary workup by addition of saturated ammonium chloride solution, the reaction mixture was extracted with ethyl acetate, and the combined organic phases were dried over Na$_2$SO$_4$ and concentrated in a membrane pump vacuum. After purification by column chromatography (ethyl acetate/cyclohexane), N,1-dimethyl-N-(pyridin-3-yl)-2-[3-(trifluoromethyl)phenyl]-1H-imidazole-5-carboxamide (212 mg, 59%) was obtained as a white solid.

mass (m/z): 360.1; $^1$H-NMR (d$^6$-DMSO): δ 8.54 (m, 1H), 8.50 (m, 1H), 7.98 (m, 2H), 7.86 (m, 2H), 7.74 (m, 1H), 7.47 (m, 1H), 6.42 (s, 1H), 3.88 (s, 3H), 3.42 (s, 3H).

The invention claimed is:

1. Method for preparing a compound of formula (II)

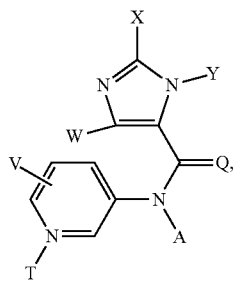

(II)

wherein
Q is oxygen,
A is a radical from the group of hydrogen, methyl, ethyl and cyclopropyl,
V is hydrogen,
T is oxygen or an electron pair,
W is a radical from the group of hydrogen, methyl, fluorine, chlorine and bromine,
Y is methyl or ethyl,
X is a radical from the group of halogen, C(O)L$^1$, C(O)OL$^1$, C(O)NL$^2$L$^3$,
  vinyl, allyl, methallyl, 2-butenyl, propargyl, ethynyl and 2-butynyl, optionally mono- to trisubstituted independently of one another by fluorine, chlorine and bromine and/or monosubstituted by methoxy, ethoxy, methylsulfanyl, ethylsulfanyl, methylsulfinyl, ethylsulfinyl, methylsulfonyl, ethylsulfonyl or cyano,
  phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano
  and straight-chain or branched phenyl-C$_1$-C$_2$-alkyl, pyridyl-C$_1$-C$_2$-alkyl, pyrimidyl-C$_1$-C$_2$-alkyl, thiazolyl-C$_1$-C$_2$-alkyl and pyrazolyl-C$_1$-C$_2$-alkyl substituted by phenyl, naphthyl, pyridyl, pyrimidyl, pyridazinyl, pyrazinyl, triazinyl, furanyl, thienyl, oxazolyl, isoxazolyl, thiazolyl, isothiazolyl, pyrazolyl, imidazolyl, oxadiazolyl, thiadiazolyl, benzofuran-2-yl or 1,2,3-triazol-4-yl, optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl, dimethylamino, diethylamino, ethylmethylamino, cyano and optionally mono- to trisubstituted independently of one another by fluorine, chlorine, bromine, methyl, ethyl, difluoromethyl, trifluoromethyl, methoxy, ethoxy, methyl-S(O)$_n$—, ethyl-S(O)$_n$—, cyclopropylmethyl-S(O)$_n$—, difluoromethoxy, trifluoromethoxy, trifluoromethyl-S(O)$_n$—, difluoroethyl-S(O)$_n$—, trifluoroethyl-S(O)$_n$—, (tetrahydro-2H-pyran-4-yloxy)methyl, dimethylsulfamoyl, methoxycarbonyl, ethoxycarbonyl, 2-ethoxy-2-oxoethoxy, (cyclopropylcarbonyl)oxy, morpholin-4-yl or cyano, wherein
L$^1$ is a radical from the group of methyl, ethyl, n- or isopropyl, 1-cyano-1-methylethyl or cyclopropyl,
L$^2$ is a radical from the group of hydrogen, methyl, ethyl, methylsulfonyl or cyclopropylsulfonyl,
L$^3$ is a radical from the group of hydrogen, methyl, ethyl, isopropyl, isobutyl, tert-butyl, 2,2,2-trifluoroethyl, 2-hydroxyethyl, 2-methoxyethyl, cyanomethyl, methoxycarbonylmethyl, ethoxycarbonylmethyl, cyclopropyl, 1-cyanocyclopropyl, cyclopentyl, cyclopropylmethyl, methoxy, ethoxy, phenyl, pyrid-3-yl, phenylmethyl, 1-phenyl-2-hydroxyethyl or
L$^2$ and L$^3$ together are (CH$_2$)$_5$, (CH$_2$)$_4$, (CH$_2$)$_3$ or (CH$_2$)$_2$O(CH$_2$)$_2$,
and n is a number 0, 1 or 2,
comprising
a) reacting a compound of formula (I)

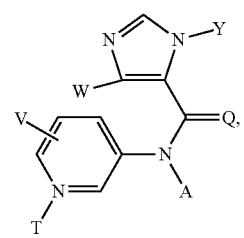

(I)

with an organozinc base of the structure (NR$^a$R$^b$)—Zn—R$^c$ or (NR$^a$R$^b$)$_2$—Zn at a temperature between 0° C. and 80° C., wherein $R^c$ is chlorine or bromine, $R^a$ and $R^b$ together form a —$(CH_2)_4$—, —$(CH_2)_5$— or —$(CH_2)_2O(CH_2)_2$— group, where each of these groups may optionally be substituted by 1, 2, 3 or 4 $R^d$ radicals and $R^d$ is selected from the group consisting of methyl, ethyl, n-propyl and isopropyl, to give a compound of formula (IIIa) or (IIIb),

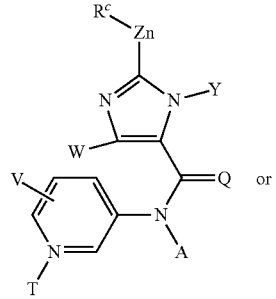
(IIIa)

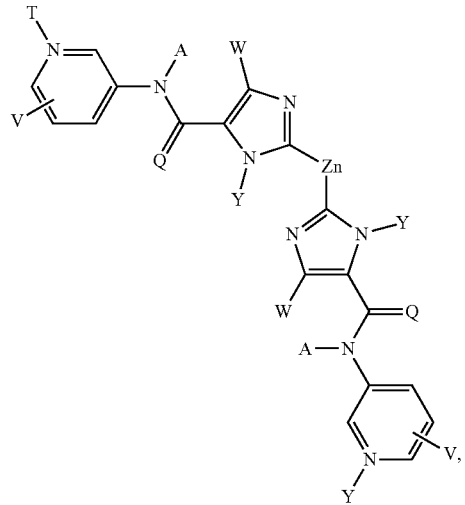
(IIIb)

and b) reacting at a temperature between −40° C. and 120° C. said compound of formula (IIIa) or (IIIb) with a compound of the structure X—Z, wherein Z is halogen to give a compound of formula (II), wherein the compounds of the formulae (I), (II), (IIIa) and (IIIb) may be present as a salt and a compound of the formulae (IIIa) and/or (IIIb) and an organozinc base may also be present complexed with a salt, wherein the organozinc base is used in a total amount of 0.5 to 5 equivalents, based on the compound of the formula (I).

2. Method according to claim 1, wherein the organozinc base is a compound of the formula (VI)

$$(TMP)_xZnCl_{2-x}, \qquad (VI)$$

in which x is the number 1 or 2.

3. Method according to claim 1, wherein the organozinc base is present in conjunction with an alkali metal halide or alkaline earth metal halide, optionally lithium chloride and/or magnesium chloride.

4. Method according to claim 1, wherein the solvent used is THF or N,N-dimethylformamide (DMF).

5. Method according to claim 1, wherein, in the compound X—Z used in b), Z is bromine or iodine.

6. Method according to claim 1, wherein the compound X—Z is used in a total amount of 0.5 to 10.0 equivalents, based on the compound of the formula (I).

7. Method according to claim 1, wherein a) takes place over a period of 10 to 90 minutes.

8. The method according to claim 1, wherein

A is methyl or ethyl,

T is an electron pair, and

W is hydrogen.

* * * * *